US012590060B2

(12) United States Patent
Slassi et al.

(10) Patent No.: US 12,590,060 B2
(45) Date of Patent: Mar. 31, 2026

(54) SCALABLE SYNTHETIC ROUTE FOR PSILOCIN AND PSILOCYBIN

(71) Applicant: Mindset Pharma Inc., St. Laurent (CA)

(72) Inventors: Abdelmalik Slassi, Mississauga (CA); Joseph Araujo, Grimsby (CA)

(73) Assignee: MINDSET PHARMA INC., St. Laurent (CA)

( * ) Notice: Subject to any disclaimer, the term of this patent is extended or adjusted under 35 U.S.C. 154(b) by 556 days.

(21) Appl. No.: 18/017,197

(22) PCT Filed: Jul. 23, 2021

(86) PCT No.: PCT/CA2021/051029
§ 371 (c)(1),
(2) Date: Jan. 20, 2023

(87) PCT Pub. No.: WO2022/016289
PCT Pub. Date: Jan. 27, 2022

(65) Prior Publication Data

US 2023/0286916 A1 Sep. 14, 2023

Related U.S. Application Data

(60) Provisional application No. 63/056,058, filed on Jul. 24, 2020.

(51) Int. Cl.
*C07D 209/16* (2006.01)
*C07D 209/18* (2006.01)
*C07F 9/572* (2006.01)

(52) U.S. Cl.
CPC ......... *C07D 209/16* (2013.01); *C07D 209/18* (2013.01); *C07F 9/5728* (2013.01)

(58) Field of Classification Search
CPC ...................................................... C07F 9/5728
See application file for complete search history.

(56) References Cited

U.S. PATENT DOCUMENTS

| | | | |
|---|---|---|---|
| 3,075,992 A | 1/1963 | Hofmann et al. |
| 3,183,172 A | 5/1965 | Heim et al. |
| 2007/0219378 A1 | 9/2007 | Hartmut et al. |

FOREIGN PATENT DOCUMENTS

| | | | |
|---|---|---|---|
| CA | 3078765 A1 | 4/2019 |
| CN | 101220054 A | 7/2008 |
| WO | 2005063777 A1 | 7/2005 |
| WO | 2010032147 A2 | 3/2010 |
| WO | 2011081937 A1 | 7/2011 |
| WO | 2019073379 A1 | 4/2019 |
| WO | 2019173797 A1 | 9/2019 |
| WO | 2023043794 A1 | 3/2023 |
| WO | 2023081829 A2 | 5/2023 |

OTHER PUBLICATIONS

Sogawa et al., Heterocycles, vol. 50, No. 2, 1999, pp. 657-660. (Year: 1999).*
Sogawa et al., "H-D Exchange of Psilocin and its Analogs", Heterocycles, vol. 50, No. 2, 1999.
Pacofsky et al., "Potent Dipeptide Inhibitors of the pp60c-src SH2 Domain", J. Med. Chem. 1998, 41, 1894-1908.
European Search report dated Jun. 26, 2024 in respect of PCT/CA2023/051019.
Search Report and Written Opinion in respect of PCT/CA2021/051029 dated Oct. 22, 2021.
Kargbo et al., "Direct Phosphorylation of Psilocin Enables Optimized cGMP Kilogram-Scale Manufacture of Psilocybin", ACS Omega 2020, 5(27), 16959-16966.
Sherwood et al., "An improved, Practical, and Scalable Five-Step Synthesis of Psilocybin", Synthesis 2020, 52, 688-694.
Hofmann A. et al., Experientia 1958, 14, 397-399.
Troxler, F. et al., Helv. Chim. Acta 1959, 42, 2073-2103.
Shirota et al., "Concise Large-Scale Synthesis of Psilocin and Psilocybin, Principal Hallucinogenic Constituents of Magic Mushroom", J. Nat. Prod. 2003, 66, 885-887.
Nichols et al., "Improvements to the Synthesis of Psilocybin and a Facile Method for Preparing the O-Acetyl Prodrug of Psilocin", Synthesis 1999, 935-938.
Yamada et al., "A five-step synthesis of psilocin from indole-3-carbaldehyde", Heterocycles 1998, 49, 457.
Sabine Berteina-Raboin et al., "A review of Synthetic Access to Therapeutic Compounds Extracted from Psilocybe", Pharmaceuticals 2023, 16, 40.

(Continued)

*Primary Examiner* — Laura L Stockton
(74) *Attorney, Agent, or Firm* — Raphael Bellum PLLC

(57) ABSTRACT

The present application relates to cost-effective, practical and scalable synthetic routes for the syntheses for psilocybin (Formula I) and its major metabolite psilocybin (Formula II) and their pharmaceutically acceptable salts. These compounds are useful for the treatment or prevention of mental health disorders, such as major depressive disorder, anxiety and addiction disorders, among others CNS disorders.

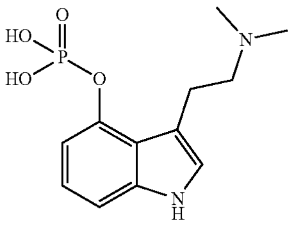

(I)

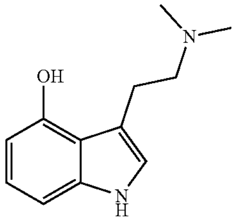

(II)

24 Claims, 8 Drawing Sheets

(56) References Cited

OTHER PUBLICATIONS

Gathergood et al., "Preparation of the 4-Hydroxytryptamine Scaffold via Palladium-Catalyzed Cyclization: A practical and Versatile Synthesis of Psilocin", Organic Letters 2003, 5, 6, 921-923.

Hofmann A. et al., Experientia 1958, 14, 397-399, English Abstract.

Troxler, F. et al., Helv. Chim. Acta 1959, 42, 2073-2103, English Abstract.

Sogawa et al., "H-D exchange of psilocin and its analogs" Heterocycles, vol. 50(2), pp. 657-660, publication date: 1999.

Pacofsky et al., "Potent Dipeptide Inhibitors of the pp60c-src SH2 Domain" J. Med. Chem., vol. 41, pp. 1894-1908, publication date: 1998.

Kargbo et al., "Direct Phosphorylation of Psilocin Enables Optimized cGMP Kilogram-Scale Manufacture of Psilocybin" ACS Omega, pp. A-H, publication date: Jun. 17, 2020.

Sherwood et al., "An Improved, Practical, and Scalable Five-Step Synthesis of Psilocybin" Synthesis, vol. 52, pp. 688-694, publication date: 2020.

Brenneisen, Rudolf, et al., "Synthesis of Baeocystin, a natural Psilocybin Analogue" Archivder Pharmazie (Dec. 31, 1988), vol. 321(8), pp. 487-489.

* cited by examiner

SCALABLE SYNTHETIC ROUTE FOR PSILOCIN AND PSILOCYBIN

CROSS REFERENCE TO RELATED APPLICATIONS

This application is a National Stage of International Application No. PCT/CA2021/051029 filled on Jul. 23, 2021 which claims the benefit of priority from U.S. provisional patent application Ser. No. 63/056,058, filed on Jul. 24, 2020, the contents of both of which are incorporated herein by reference in their entirety.

FIELD OF THE DISCLOSURE

The present invention relates to scalable processes for preparing psilocybin (4-phosphoryloxy-N,N-dimethyltryptamine) and its major metabolite psilocin (4-hydroxy-N,N-dimethyltryptamine), as well as their pharmaceutically acceptable salts.

BACKGROUND

Psilocybin, (4-phosphoryloxy-N,N-dimethyltryptamine, also known as psilocin phosphate ester) is a prodrug that has the chemical formula $C_{12}H_{17}N_2O_4P$, has exact molecular weight of 284.092594 g/mol, contains three (3) hydrogen bond donors, five (5) hydrogen bond acceptor counts, a the polar surface area (PSA) or topological polar surface area (TPSA) of 85.8 $Å^2$ (Formula I). When consumed via the oral route, psilocybin is rapidly dephosphorylated by alkaline phosphatase in the gut to psilocin [Dinis-Oliveira, R. J. Drug Metab. Rev. 2017, 49, 84-91]. Psilocin, (4-hydroxy-N,N-dimethyltryptamine) also known as 4-OH-DMT, is the most prominent active metabolite of psilocybin, which is capable of penetrating the blood brain barrier (BBB) and interacts with 5-$HT_{2A}$ receptors, among other targets, to produce psychedelic effects. Its chemical formula $C_{12}H_{16}N_2O$, has exact molecular weight of 204.126263 g/mol, contains two (2) hydrogen bond donors, two (2) hydrogen bond acceptor counts, and a TPSA of 39.3 $Å^2$ (Formula II).

The chemical structures of psilocybin and psilocin are fairly simple and achiral, and they are closely related to the neurotransmitter serotonin [5-hydroxytryptamine (5-HT)].

Psilocybin has been shown to have much medicinal therapeutic potential value, for example, in psychedelic-assisted therapy in psychiatric illnesses and disorders, opioid use disorder (OUD), sleep disturbances, anxiety disorders, major depressive disorder and cancer-related psychiatric distress and as a hallucinogenic. Its therapeutic value combined with its increasing worldwide popularity as a recreational drug, warrants the need for more rigorous research with psilocybin. Consequently, scientific research efforts have increased to create a more cost-effective and reproducible method for the production of psilocybin. Specifically, there is high demand for investigational substances that are suitably pure for human use and that can be prepared in a relatively economical fashion.

Currently, psilocybin may be produced using one of three different methods (i) by biological processes, such as by fermentation, (ii) by extraction from magic mushrooms, or (iii) by organic synthetic methods.

Psilocybin can be extracted from natural sources, as it is bio-synthesized in certain species of mushrooms. However, this method relies on the supply of the mushrooms, whose production could be inconsistent and difficult to control. Furthermore, its production in sufficient and pure amounts for use in human trials from the extraction of naturally occurring mushrooms is quite difficult due to its stability, as psilocybin easily decomposes to its major metabolite psilocin which has a high polarity, therefore this method is not a useful production for the drug. In addition, the reported yields of psilocybin are typically very low from natural sources, e.g., 0.85% of the dry mass for *Psilocybe serbica*, approximately 1.0% for *P. semilanceata*, and around 1.5-1.8% in *P. azurescens* [Tyls, T. et al. Eur. Neuropsychopharm. 2014, 24, 342-356; Hoffmeister, Chem. Eur. J. 2019, 25, 897-903]. Therefore, this method is not a useful production for the commercial manufacturing of psilocybin for therapeutic use.

Alternatively, biosynthetic psilocybin production using enzymes derived from psilocybin-containing fungi has only recently been identified and is outlined in four steps (Scheme 1) via biochemical transformation from L-tryptophan (A) which involves several enzyme reactions: decarboxylation leads to tryptamine (B); dimethylation of the amine of the ethylamine side-chain provides N,N-dimethyltryptamine (C); 4-hydroxylation via oxidation leads to 4-hydroxytryptamine, psilocin, (II); and subsequent O-phosphorylation yields psilocybin (I) [Fricke, J. et al., Angew. Chem., Int. Ed. 2017, 56, 12352-12355].

Scheme 1: Biosynthetic route of psilocin (II) and psilocybin (I)

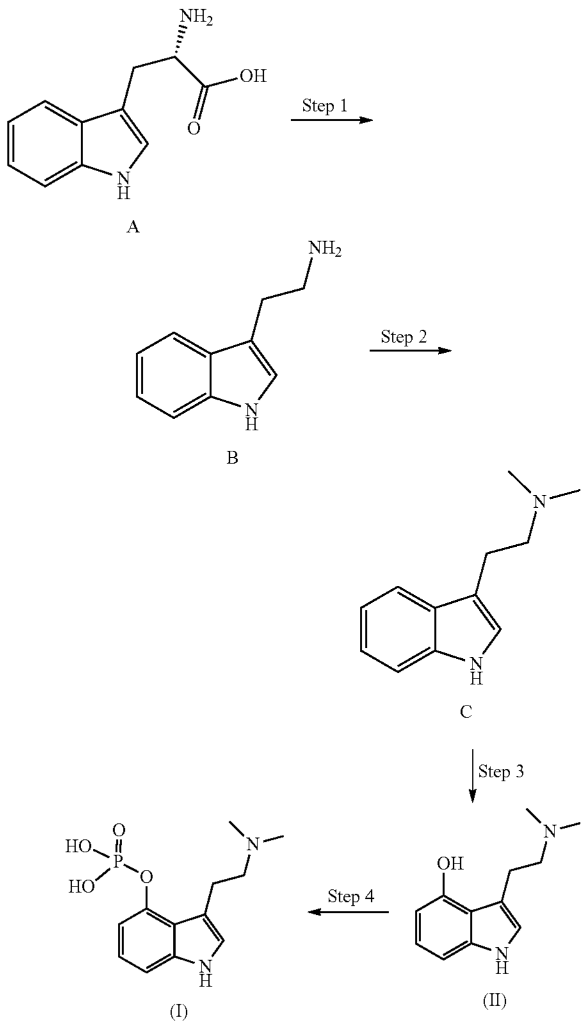

A

B

C (II)

(I)

Recent analyses of isolated enzymes demonstrates that 0-phosphorylation is the third step in *P. cubensis*. The sequence of the intermediate enzymatic steps has been shown to involve 4 different enzymes (PsiD, PsiH, PsiK, and PsiM) in *P. cubensis* and *P. cyanescens*, although the biosynthetic pathway may differ between species. These enzymes are encoded in gene clusters in *Psilocybe, Panaeolus*, and *Gymnopilus* [Fricke J. et al. (Angew. Chem., 2017, 56(40): 12352-12355; Reynolds H, et al., Evolution Letters. 2018, 2 (2): 88-101].

In more recent work, another modular biosynthetic psilocybin production platform was developed in the model microbe, *Escherichia coli*. Efforts to optimize and improve pathway performance using multiple genetic optimization techniques were evaluated, resulting in a 32-fold improvement in psilocybin titer. Further enhancements to this genetically superior strain were achieved through fermentation optimization, ultimately resulting in a fed-batch fermentation study, with a production titer of 1.16 g/L of psilocybin for use in ongoing clinical trials [Adams et al. Metabolic Engineering, 2019, 56, 111-119].

Alternatively, this biosynthetic process may also begin from 4-hydroxy-L-tryptophan, which undergoes decarboxylation via PsiD to yield 4-hydroxytryptamine, and the biosynthesis of psilocybin continues from this point as in Scheme 1 [Fricke, J. et al., Angew. Chem., Int. Ed. 56, 2017, 12352-12355].

Similarly, it was recently reported that two enzymes from *Psilocybe cubensis* carry out a two-step cascade to prepare psilocybin for oxidative oligomerization that leads to blue products. The phosphatase PsiP removes the 4-O-phosphate group to yield psilocin, while PsiL oxidizes its 4-hydroxy group. The PsiL reaction was monitored by in situ $^{13}C$ NMR spectroscopy, which indicated that oxidative coupling of psilocyl residues occurs primarily via C-5. MS and IR spectroscopy indicated the formation of a heterogeneous mixture of preferentially psilocyl 3- to 13-mers and suggest multiple oligomerization routes, depending on oxidative power and substrate concentration. The results also imply that phosphate ester of psilocybin serves a reversible protective function [Claudius L. et al., Angew. Chem. Int. Ed. 2020, 59, 1450-1454]

International patent application WO2019/180309 discloses an enzymatic pathway for biosynthesis of psilocybin. The pathway uses amino-acid L-tryptophan as an initial substrate. L-tryptophan is converted into tryptamine and $CO_2$ in the first enzymatic reaction catalysed by the PsiD enzyme. Tryptamine is converted into 4-hydroxytryptamine in the second enzymatic reaction catalysed by the PsiH enzyme, where oxygen is used in the reaction to form the hydroxyl-group. 4-hydroxytryptamine is converted into norbaeocystin in the third enzymatic reaction catalysed by the PsiK enzyme, where adenosine triphosphate (ATP) is used as a donor of the phosphate group. Norbaeocystin is converted into baeocystin and eventually psilocybin in the fourth and fifth enzymatic reactions catalysed by the PsiM enzyme, where S-adenosyl methionine (SAM) is used as a donor of the methyl groups. Psilocybin can be converted into psilocin in a reaction catalysed either by a native host phosphatase, or spontaneously. It can be re-phosphorylated by the PsiK enzyme to form psilocybin again.

Psilocybin can also be prepared synthetically. In fact, its original synthetic process was reported by Hofmann and co-worker as shown in Scheme 2 [Hofmann, A. et al. Experientia 1958, 14, 397-399; Helv. Chim. Acta 1959. 42, 2073-2103]. The synthesis begins with benzylation of 4-hydroxyindole (E) leading to benzyl protected 4-hydroxyindole (F), which is treated with oxalyl chloride and dimethyl amine to produce 2-(4-(benzyloxy)-1H-indol-3-yl)-N,N-dimethyl-2-oxoacetamide (G). Subsequently, the product is reduced with lithium aluminum hydride to provide benzyl protected psilocin (H). Deprotection under hydrogen gas with palladium on carbon gives psilocin (II). This product then undergoes phosphorylation with O,O-dibenzyl phosphoryl chloride to yield benzyl protected psilocybin (IIa). De-benzylation under hydrogen gas with palladium on carbon gives the final product, psilocybin (I) [Hofmann, A. et al. Experientia 1958, 14, 397-399; Helv. Chim. Acta 1959. 42, 2073-2103].

Scheme 2: Original Synthetic Process for the Synthesis of psilocin (II) and psilocybin (I) as reported by Hofmann

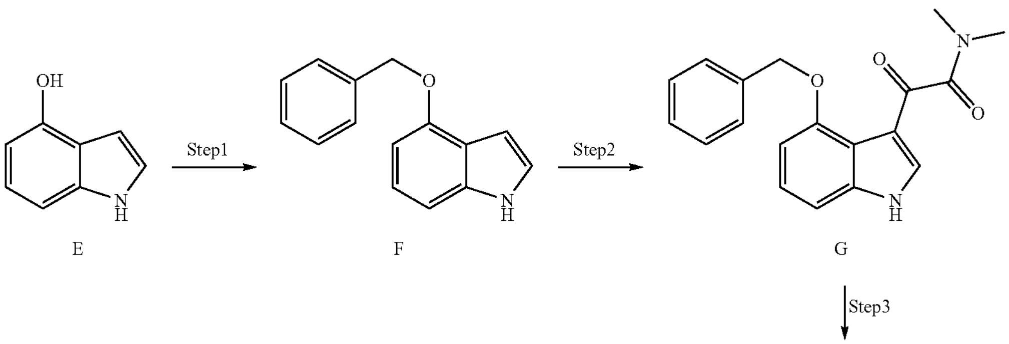

E F G

-continued

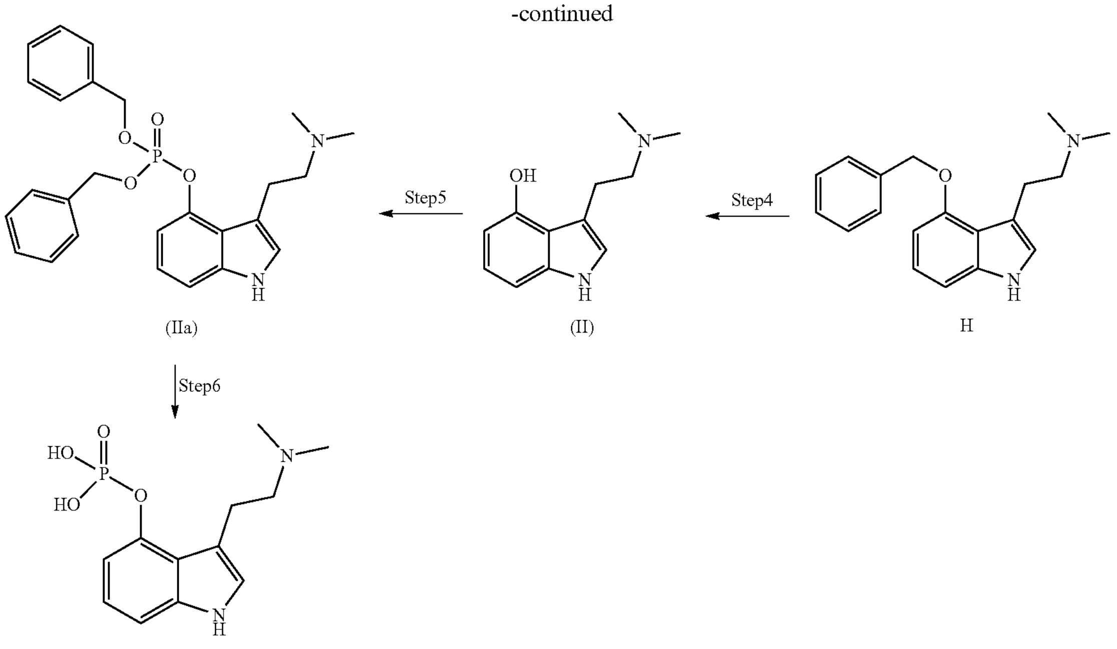

(IIa) (II) H (I)

Hofmann's synthesis has since been modified by various groups who have made numerous contributions to the process to improve overall purity and yield. For instance, recently, it was shown that during synthesis of psilocybin (1), a by-product was formed by the spontaneous intramolecular migration of one of the benzyl groups on (IIa) to form the corresponding zwitterionic N,O-dibenzyl phosphate derivative (IIb) from the O,O-dibenzyl phosphate derivative (IIa) (Scheme 3) [Shirota, O. et al., J. Nat. Prod. 2003, 66, 885-887].

Scheme 3

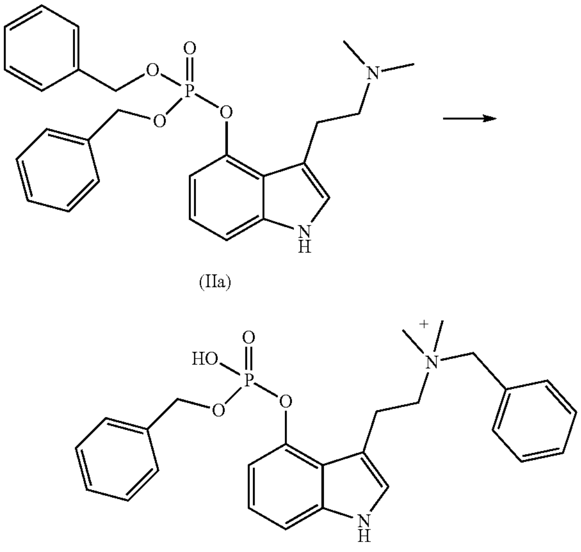

(IIa)

(IIb)

An improved procedure to accomplish the O-phosphorylation of 4-hydroxy-N,N-dimethyltryptamine, psilocin (II), has been reported that utilizes reaction between the O-lithium salt of indole moiety, by using n-butyllithium as base, and tetra-O-benzylpyrophosphate. The O-benzyl groups were then removed by catalytic hydrogenation over palladium on carbon to afford psilocybin. In view of difficulties encountered in the preparation of psilocybin, it has been suggested that 4-acetoxy-N,N-dimethyltryptamine may be a useful alternative for pharmacological studies. The latter was obtained following catalytic O-debenzylation of 4-benzyloxy-N,N-dimethyltryptamine in the presence of acetic anhydride and sodium acetate [Nichols, D. et al., Synthesis 1999, 935-938].

A slightly improved process for the preparation of psilocybin (I) is disclosed in International patent application WO2019/073379 based on the same synthetic route developed by Hoffmann and co-workers but using an acetoxy-indole as starting material instead of benzyloxy-indole, Similarly, a recent small-scale synthesis of psilocybin (I) has been disclosed without the use of chromatography or aqueous workup in five steps that results in 23% overall yield [Sherwood A. M. *Synthesis* 2020, 52, 688-694].

A kilogram-scale synthesis of psilocybin (I) has also been disclosed wherein psilocin is phosphorylated directly with phosphorous oxychloride without the use of protecting groups [Sherwood et at on ACS Omega 2020, 5, 27, 16959-16966].

Another synthesis of 4-hydroxyindoles from indole via 4-iodoindoles using thallium acetate has been reported which was used to prepare psilocin (II) [Yamada. F. et al., M. *Heterocycles* 1998, 49, 451].

A method for the preparation of psilocin (II) avoiding the use of thallium salts, from N-tert-butoxycarbonyl-2-iodo-3-methoxyaniline (J) in three steps has also been reported (Scheme 4).

Scheme 4

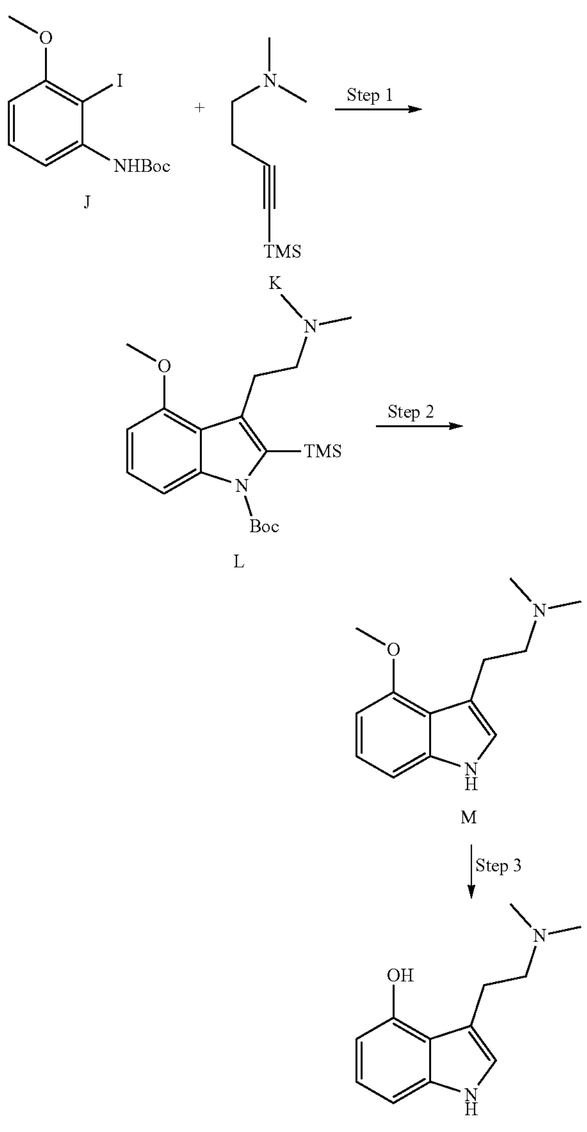

J K L M (II)

The key step in the above process is the formation of the indole core via a palladium-catalyzed cyclization. The two fragments required for the cyclization are (J) and alkyne (K). Intermediate (J) was prepared according to literature procedure from Boc-protected 3-methoxyaniline, via directed lithiation and iodination [Snieckus V. *Chem. ReV.* 1990, 90, 879]. The preparation of (K) was achieved from 3-butyn-1-ol as previously reported [Smith, A. L. GB2328941, 1999]. Tosylation, substitution with N,N-dimethylamine, and treatment with n-butyllithium, trimethylsilyl chloride gave the required alkyne. The key palladium-catalyzed cyclization step was obtained using $Pd(OAc)_2$, triphenylphosphine, tetraethylammonium chloride, and N,N-diisopropylethylamine in DMF at 80° C. for 48 h.

To complete the synthesis of psilocin, the Boc and trimethylsilyl groups of (L) were cleaved by treatment with neat TFA to afford (M) which was subjected to O-Demethylation using boron tribromide yielded psilocin (II) [Scammells P. J. et al. *Org. Lett.,* 5, 6, 2003].

The main drawback in this latter synthesis is the handling of the costly and corrosive iodine intermediate, and hazardous and costly butyl lithium. Palladium acetate is very expensive. Also, 3-butyn-1-ol, used in the process is expensive and not readily available on commercial scale. Purity of psilocin, the precursor of psilocybin, is poor and required multiple column chromatography processes for purification. Therefore, the method is not viable for commercial production of psilocybin.

Keeping in view of the difficulties in commercialization of the above-mentioned processes for the preparation of psilocin and psilocybin, there is a need to develop simple and economical processes for commercial production of psilocin and/or psilocybin.

SUMMARY

The Applicant has developed novel, cost-effective, practical and scalable routes for the preparation of psilocybin (compound of Formula I) which is (4-phosphoryloxy-N,N-dimethyltryptamine) and for its major metabolite psilocin (compound of Formula II) which is (4-hydroxy-N,N-dimethyltryptamine).

Accordingly, the present application includes a process for preparing psilocin (compound of Formula II):

(II)

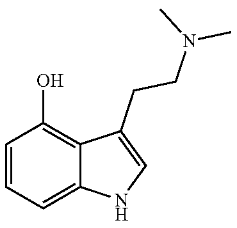

the process comprising:

reacting unprotected 4-hydroxyindole (compound of Formula III):

(III)

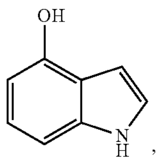

, with oxalyl chloride to provide a compound of Formula (IV):

(IV)

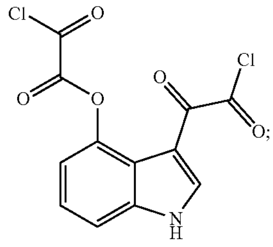

;

reacting the compound of Formula (IV) with dimethylamine ($HN(CH_3)_2$) to provide a compound of Formula V:

(V)

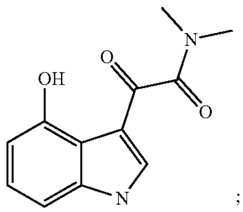

;

and reducing the compound of Formula (V) with a reducing reagent to provide psilocin (compound of Formula II).

The present application also includes a process for preparing psilocybin (compound of Formula I):

(I)

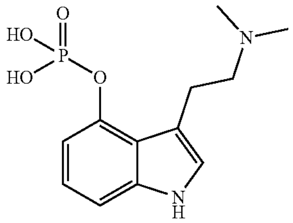

the process comprising:

reacting psilocin (compound of Formula II):

(II)

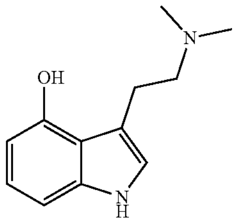

with (a) di-tert-butylphosphite,

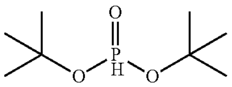

in the presence of a base or (b) chloro di-tert-butylphosphite,

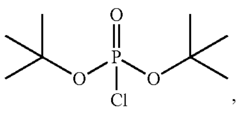

, to provide a compound of Formula (VI):

(VI)

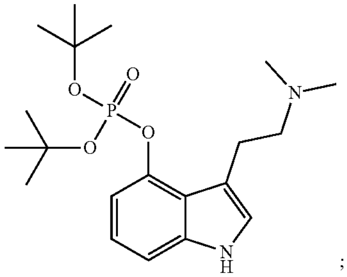

;

and hydrolyzing the compound of Formula VI to provide the psilocybin (compound of Formula I).

The present application also includes a process for preparing psilocin (compound of Formula II):

(II)

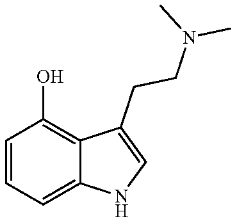

the process comprising:

reacting unprotected 4-hydroxyindole (compound of Formula III):

(III)

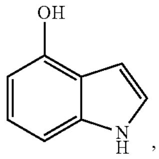

, with oxalyl chloride to provide a compound of Formula (IV):

(IV)

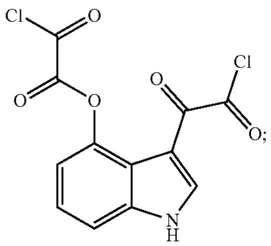

reacting the compound of Formula (IV) with dimethylamine ($HN(CH_3)_2$) to provide a compound of Formula V:

(V)

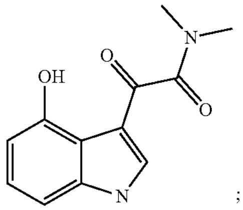

;

and reducing the compound of Formula (V) with a reducing reagent to provide psilocin (compound of Formula II).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

I. Definitions

Figure 1:
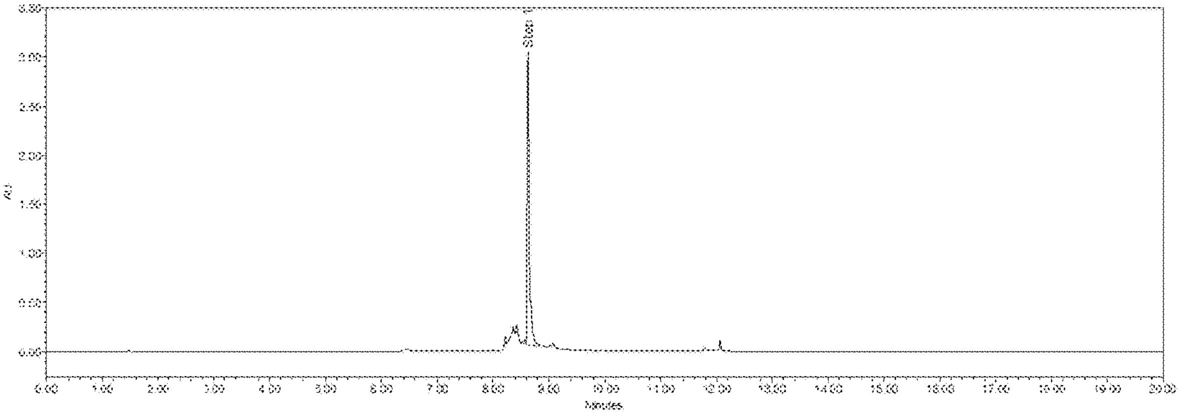
FIG. 1 shows an HPLC chromatogram of the compound of Formula IV.

Unless otherwise indicated, the definitions and embodiments described in this and other sections are intended to be applicable to all embodiments and aspects of the present application herein described for which they are suitable as would be understood by those skilled in the art.

The term "process of the application" and the like as used herein refers to a process of preparing psilocybin, psilocin, an acid salt of psilocybin, and/or an acid salt of psilocin as described herein.

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a solvent" should be understood to present certain aspects with one solvent, or two or more additional solvents.

In embodiments comprising an "additional" or "second" component, such as an additional or second solvent, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions to provide the product shown. A person skilled in the art would understand that, unless otherwise indicated, all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word.

The present description refers to a number of chemical terms and abbreviations used by those skilled in the art. Nevertheless, definitions of selected terms are provided for clarity and consistency.

The term "available", as in "available hydrogen atoms" or "available atoms" refers to atoms that would be known to a person skilled in the art to be capable of replacement by a substituent.

The term "psilocybin" or "compound of Formula I" or "(I)" as used herein refers to a compound having the IUPAC name: 3-[2-(dimethylamino)ethyl]-1H-indol-4-yl dihydrogen phosphate or the chemical name 4-phosphoryloxy-N,N-dimethyltryptamine and having the chemical formula:

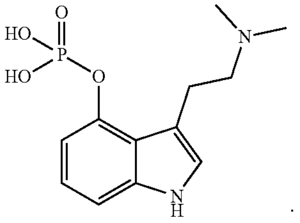 [SMILES: CN(C)CCc1c[nH]c2cccc(OP(=O)(O)O)c12]

The term "psilocin" or "compound of Formula II" or "(II)" as used herein refers to a compound having the IUPAC name: 4-hydroxy-N,N-dimethyltryptamine and having the chemical formula:

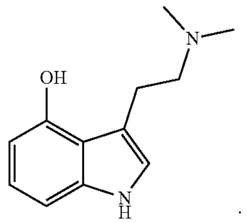

The term "reducing agent" as used herein means any compound or combination of compounds that reduces a desired functional group. A reducing agent results in the overall addition of electrons, or in the case of organic chemistry, hydrogen atoms to the functional group.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art.

The term "solvent" includes both a single solvent and a mixture comprising two or more solvents.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "Atherton-Todd reaction" as used herein refers to a reaction for the conversion of dialkyl phosphites into dialkyl chlorophosphates through the reaction of tetrachloromethane (carbon tetrachloride) in the presence of a base, first described by F. R. Atherton, H. T. Openshaw and A. R. Todd in 1945 (Journal of the Chemical Society, pp. 660-663). The base is usually a primary, secondary or tertiary amine.

The products of the processes of the application may be isolated according to known methods, for example, the compounds may be isolated by evaporation of the solvent, by filtration, centrifugation, chromatography or other suitable method.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound.

The term "subject" as used herein includes all members of the animal kingdom including mammals, and suitably refers to humans.

II. Processes of the Application

The Applicant has developed novel cost-effective, practical and scalable routes of syntheses for psilocybin (compound of Formula I) which is 4-phosphoryloxy-N,N-dimethyltryptamine and for its major metabolite psilocin (compound of Formula II) which is 4-hydroxy-N,N-dimethyltryptamine. The processes of the application provide a novel method for the preparation of highly pure psilocybin or psilocin and can be easily adopted for commercial production with a high degree of consistency in purity and yield. The prepared psilocybin or psilocin can subsequently be converted into any suitable pharmaceutically acceptable salt, such as the oxalate, succinate or benzoate salt, for dosage form preparation.

The new synthetic routes of preparing psilocybin and psilocin of the application have several advantages, such as (i) mild reaction conditions, (ii) convenient operations, (iii) easily obtained commercially available raw materials, and (iv) suitability for multi-kilogram scale manufacturing. A further advantage is the ability to produce psilocybin and psilocin with improved yields, purity and reproducibility.

Starting from unprotected 4-hydroxytryptamine, psilocybin (Formula I) can be synthesized through a five-step procedure via psilocin (Formula II) starting with the condensation of 4-hydroxyindole directly with oxalyl chloride. The Applicant has surprisingly found that this condensation step can be affected without the need for any protecting groups on the OH of the 4-hydroxyindole, for example, by reacting oxalyl chloride directly with the unprotected 4-hydroxyindole in an organic solvent such as methyl tert-butyl ether (MTBE) or diethyl ether to provide a di 2-chloro-2-oxoacetyl intermediate (compound of Formula IV). Reacting unprotected 4-hydroxyindole directly with oxalyl chloride advantageously avoids the 4-hydroxyindole protection and subsequent deprotections steps used in the processes for synthesizing psilocin or psilocybin known in the art, for example, the processes described above, and further avoids the production of undesired by-products resulting from the additional protection and deprotection steps. Further advantageously, the compound of Formula IV can be used in the subsequent reaction steps without direct isolation or purification, i.e., the product of the condensation step (compound of Formula IV) can be telescoped into the subsequent reaction with dimethylamine to provide an oxoacetamide compound of Formula V. The compound of Formula V is then reduced with, for example, lithium aluminum hydride to provide psilocin.

The Applicant has further surprisingly found that psilocin can be transformed to psilocybin via a new optimized phosphorylation reaction using di-tert-butylphosphite as the phosphorylating reagent to provide a di-tert-butylphosphite compound of Formula VI. For example, psilocin can be phosphorylated using di-tert-butylphosphite in the presence of a base, such as sodium hydroxide, or sodium hydroxide in combination with 4-dimethylaminopyridine (DMAP) in an inert solvent such as a mixture of carbon tetrachloride and tetrahydrofuran (THF). Alternatively, psilocin can be phosphorylated using chloro di-tert-butyl phosphite which, for example, can be generated in situ by combining di-tert-butylphosphite in the presence of N-chloro succinimide. The latter option further advantageously avoids the use of carbon tetrachloride as required in the Atherton-Todd reaction. The resultant di-tert-butylphosphite compound of Formula VI is then simply hydrolyzed with acid to provide psilocybin. Advantageously again, the di-tert-butylphosphite compound of Formula VI can be telescoped into the subsequent hydrolysis step with direct isolation. Further, the use of di-tert-butylphosphite as the phosphorylating reagent instead of the O,O-dibenzyl phosphite type reagent used in the art (for example, see Hofmann, A. et al. Experientia 1958, 14, 397-399; Helv. Chim. Acta 1959. 42, 2073-2103 and Shirota, O. et al., J. Nat. Prod. 2003, 66, 885-887) advantageously avoids the formation of the problematic zwitterionic N,O-dibenzyl phosphate derivative by-product (see IIb described above) generated when removing the benzyl groups introduced with the O,O-dibenzyl phosphite type phosphorylating reagents. Instead, the di-tert-butyl groups introduced by the di-tert-butylphosphite reagent as described herein is efficiently removed by hydrolysis with acid.

The Applicant has confirmed the authenticity of the chemical structures of both psilocybin and its metabolite psilocin by, for example, $^{1}H$ NMR, $^{13}C$ NMR, IR, HPLC and/or LCMS.

The novel routes of syntheses of the application have such advantages as improved yield, purity and reproducibility, mild reaction conditions, and are environmentally friendly.

As the Applicant has found that psilocin can be transformed into psilocybin via a new optimized phosphorylation reaction with di-tert-butylphosphite, the present application includes a process for preparing psilocybin (compound of Formula I):

(I)

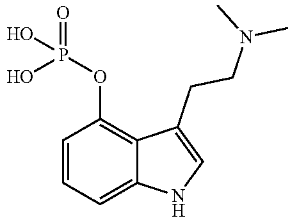

the process comprising:

reacting unprotected psilocin (compound of Formula II):

(II)

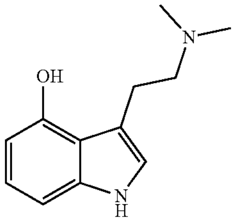

with (a) di-tert-butylphosphite,

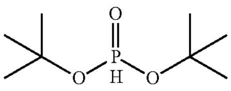

in the presence of a base or (b) chloro di-tert-butylphosphite,

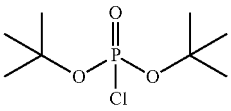

to provide a compound of Formula (VI):

(VI)

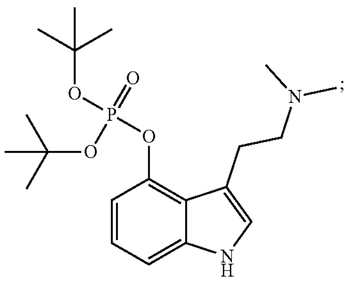

and hydrolyzing the compound of Formula VI to provide the psilocybin (compound of Formula I).

As the Applicant has found that psilocin can be prepared, for example, by reacting unprotected 4-hydroxyindole directly with oxalyl chloride, the present application also includes a process for preparing psilocin (compound of Formula II):

(II)

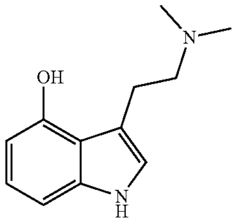

the process comprising:

reacting unprotected 4-hydroxyindole (compound of Formula III):

(III)

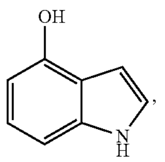

with oxalyl chloride to provide a compound of Formula (IV):

(IV)

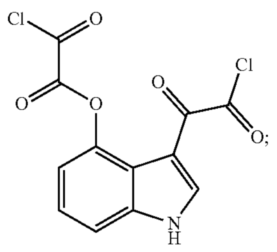

reacting the compound of Formula (IV) with dimethylamine ($HN(CH_3)_2$) to provide a compound of Formula V:

(V)

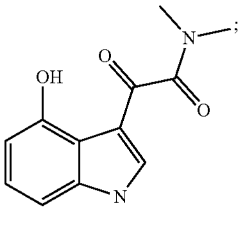

and reducing the compound of Formula (V) with a reducing reagent to provide psilocin (compound of Formula II).

Therefore, the Applicant has found that starting from unprotected 4-hydroxytryptamine, psilocybin (Formula I) can be synthesized through a five-step procedure via psilocin. Accordingly, the present application includes a process for preparing psilocybin (compound of Formula I):

(I)

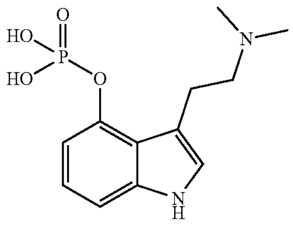

the process comprising:

reacting unprotected 4-hydroxyindole (compound of Formula III):

(III)

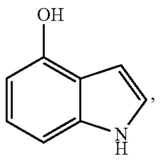

with oxalyl chloride to provide a compound of Formula (IV):

(IV)

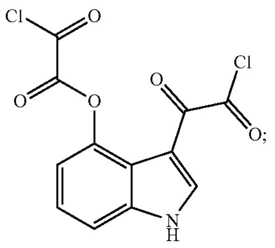

reacting the compound of Formula (IV) with dimethylamine ($HN(CH_3)_2$) to provide a compound of Formula (V):

(V)

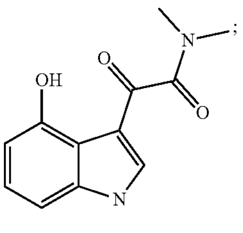

reducing the compound of Formula (V) with a reducing reagent to provide psilocin (compound of Formula II);

(II)

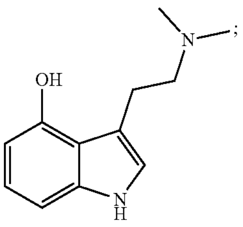

reacting psilocin with (a) di-tert-butylphosphite,

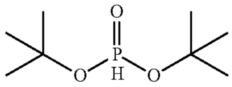

in the presence of a base, or (b) chloro di-tert-butylphosphite,

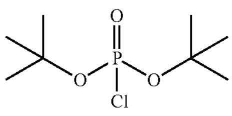

to provide a compound of Formula (VI):

(VI)

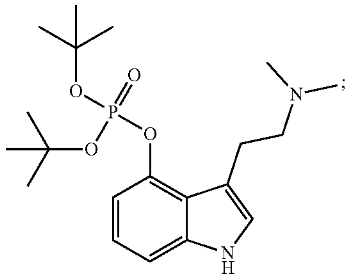

and hydrolyzing the compound of Formula (VI) provide psilocybin (compound of Formula I).

In some embodiments, the unprotected 4-hydroxyindole (compound of Formula III) is reacted with an excess amount of oxalyl chloride to provide the compound of Formula (IV). In some embodiments, the unprotected 4-hydroxyindole (compound of Formula III) is reacted with an excess amount (for example, about 2 to about 5 molar equivalents, about 2 to about 4 molar equivalents, about 2 to about 3 molar equivalents, about 3 to about 5 molar equivalents, about 3 to about 4 molar equivalent about 3 molar equivalents or about 2.2 molar equivalents) of oxalyl chloride to provide the compound of Formula (IV). In some embodiments, the unprotected 4-hydroxyindole (compound of Formula III) is reacted with an excess amount (for example, about 2 to about 4 molar equivalents, about 3 molar equivalents or about 2.2 molar equivalents) of oxalyl chloride to provide the compound of Formula (IV).

In some embodiments, the reacting of the unprotected 4-hydroxyindole (compound of Formula III) with an excess amount of oxalyl chloride to provide the compound of Formula (IV) comprises adding the unprotected 4-hydroxyindole (compound of Formula III) to an excess amount of oxalyl chloride in an inert solvent for a temperature and a time for the reaction of unprotected 4-hydroxyindole with oxalyl chloride to provide the compound of Formula (IV). In some embodiments, the reacting of the unprotected 4-hydroxyindole (compound of Formula III) with an excess amount of oxalyl chloride to provide the compound of Formula (IV) comprises adding the excess amount of oxalyl chloride to the unprotected 4-hydroxyindole (compound of Formula III) in an inert solvent for a temperature and a time for the reaction of unprotected 4-hydroxyindole with oxalyl chloride to provide the compound of Formula (IV). In some embodiments, the inert solvent is selected from ethers such as diethyl ether, methyl tert-butyl ether (MTBE) and tetrahydrofuran, esters such as ethyl acetate, hydrocarbon solvents such as toluene, and halogenated solvents such as methylene chloride and carbon tetrachloride, and mixtures thereof. In some embodiments, the inert solvent is selected from diethyl ether, methyl t-butyl ether, tetrahydrofuran, ethyl acetate, toluene, methylene chloride and carbon tetrachloride, and mixtures thereof. In some embodiments, the inert solvent is diethyl ether or MBTE. In some embodiments, the inert solvent MBTE. In some embodiments, the reacting of the unprotected 4-hydroxyindole (compound of Formula III) with an excess amount of oxalyl chloride to provide the compound of Formula (IV) comprises adding the unprotected 4-hydroxyindole (compound of Formula III) to an excess amount of oxalyl chloride in an inert solvent such as diethyl ether or MTBE for a temperature and a time for the reaction of unprotected 4-hydroxyindole with oxalyl chloride to provide the compound of Formula (IV). In some embodiments, the inert solvent is diethyl ether. In some embodiments, the reacting of the unprotected 4-hydroxyindole (compound of Formula III) with an excess amount of oxalyl chloride to provide the compound of Formula (IV) comprises adding the excess amount of oxalyl chloride to the unprotected 4-hydroxyindole (compound of Formula III) in diethyl ether for a temperature and a time for the reaction of unprotected 4-hydroxyindole with oxalyl chloride to provide the compound of Formula (IV).

As representative, non-limiting examples, the temperature and times for reacting the unprotected 4-hydroxyindole (compound of Formula III) with oxalyl chloride to provide the compound of Formula (IV) is about 0° C. to about 15° C., about 0° C. to about 10° C., about 5° C. to about 10° C. or about 0° C. to about 5° C. for about 6 hours to about 24 hours, about 10 hours to about 20 hours, about 12 hours to about 20 hours, about 14 hours to about 18 hours or about 16 hours. In some embodiments, the temperature and times for reacting the unprotected 4-hydroxyindole with oxalyl chloride to provide the compound of Formula (IV) is about 0° C. to about 10° C., about 5° C. to about 10° C. or about 0° C. to about 5° C. for about 12 hours to about 20 hours, about 14 hours to about 18 hours or about 16 hours.

Accordingly, in some embodiments the process comprises reacting unprotected 4-hydroxyindole with about 3 to about 5 molar equivalents, about 3 to about 4 molar equivalent or about 3 molar equivalents of oxalyl chloride in an inert solvent at a temperature of about 0° C. to about 5° C. for about 14 hours to about 18 hours or about 16 hours to provide the compound of Formula (IV). In some embodiments the process comprises reacting unprotected 4-hydroxyindole with about 3 to about 5 molar equivalents, about 3 to about 4 molar equivalent or about 3 molar equivalents of oxalyl chloride in diethyl ether at a temperature of about 0° C. to about 5° C. for about 14 hours to about 18 hours or about 16 hours to provide the compound of Formula (IV).

In some embodiments the process comprises reacting unprotected 4-hydroxyindole with for example, about 2 to about 4 molar equivalents, about 2 to about 3 molar equivalents, or about 2.2 molar equivalents oxalyl chloride in an inert solvent such as MTBE at a temperature of about 0° C. to about 10° C. or about 5° C. to about 10° C. for a time of about 1 hours to about 4 hours or about 2 hours to about 3 hours to provide the compound of Formula (IV). In some embodiments the process comprises reacting unprotected 4-hydroxyindole with for example, about 2 to about 3 molar equivalents, or about 2.2 molar equivalents oxalyl chloride in an inert solvent such as MTBE at a temperature of about 5° C. to about 10° C. or ab 5° C. for about 2 hours to about 3 hours to provide the compound of Formula (IV).

In some embodiments, the dimethylamine ($N(CH_3)_2$) is generated in situ by reacting a dimethylamine acid salt such as dimethylamine hydrochloride with a base. Accordingly, in some embodiments, the compound of Formula (IV) is reacted with dimethylamine acid salt in the presence of a base to provide the compound of Formula (V). In some embodiments, the compound of Formula (IV) is reacted with dimethylamine hydrochloride ($N(CH_3)_2 \cdot HCl$) in the presence of a base to provide the compound of Formula (V). In some embodiments, the base is an organic amine base. In some embodiments, the organic amine base is selected from pyridine, triethylamine, trimethylamine, triphenylamine, tripropylamine, tripentylamine, tert-butylamine, cyclohexylamine, cyclooctylamine, pentylamine or octylamine. In some embodiments, the organic amine base is triethylamine or pyridine. In some embodiments, the organic amine base is triethyl amine. In some embodiments, organic amine base is pyridine.

In some embodiments, the compound of Formula (IV) is reacted with an excess amount of the dimethylamine acid salt in the presence of the base to provide the compound of Formula (V). In some embodiments, the compound of Formula (IV) is reacted with about 2 to about 6 molar equivalents, about 3 to about 5 molar equivalents, about 3 molar equivalents, about 4 molar equivalents, about 5 molar equivalents or about 6 molar equivalents of the dimethylamine acid salt in the presence of the base to provide the compound of Formula (V). In some embodiments, the compound of Formula (IV) is reacted with about 3 to about 5 molar equivalents, about 3 molar equivalents, about 4 molar equivalent or about 5 molar equivalents of the dimethylamine acid salt in the presence of the base to provide a compound of Formula (V). In some embodiments, the compound of Formula (IV) is reacted with about 3 to about 5 molar equivalents, or about 5 molar equivalents of the dimethylamine acid salt in the presence of the base to provide the compound of Formula (V).

In some embodiments, the compound of Formula (IV) is reacted with an excess amount of dimethylamine acid salt in the presence of the base in an inert solvent for a temperature and a time for the compound of Formula (IV) to react with the dimethylamine acid salt in the presence of the base to provide the compound of Formula (V). In some embodiments, the inert solvent is selected from ethers such as diethyl ether and tetrahydrofuran, esters such as ethyl acetate, hydrocarbon solvents such as toluene, and halogenated solvents such as methylene chloride and carbon tetrachloride, and mixtures thereof. In some embodiments, the inert solvent is diethyl ether. In some embodiments, the base is an organic amine base that is a liquid at room temperature, such as pyridine. In an embodiment, the base is present in an amount to neutralize the dimethylamine acid salt, i.e. to convert the acid salt to the free base. In some embodiments, the base is present in excess amounts relative to both the compound of Formula (IV) and the dimethylamine acid salt. In some embodiments, the base is used as a solvent or co-solvent.

As representative, non-limiting examples, the temperature and times for reacting the compound of Formula (IV) with the dimethylamine acid salt in the presence of the base to provide the compound of Formula (V) is about 18° C. to about 25° C., about 20° C. to about 25° C. or room temperature for about 15 minutes to about 2 hours, about 15 minutes to about 1 hour, about 15 minutes to about 45 minutes, about 30 minutes to about 45 minutes or about 30 minutes.

Accordingly, in some embodiments, the compound of Formula (IV) is reacted with about 3 to about 5 molar equivalents, or about 5 molar equivalents of the dimethylamine acid salt in the presence of the base at room temperature for about 30 minutes to about 45 minutes or about 30 minutes to provide the compound of Formula (V).

In some embodiments, the compound of Formula (IV) that is reacted with the dimethylamine acid salt in the presence of the base to provide the compound of Formula (V) is crude or not purified, or the compound of Formula (V) is not isolated before reacting with the dimethylamine acid salt in the presence of the base to provide a compound of Formula (V).

In some embodiments, the compound of Formula (IV) is reacted with dimethylamine to provide the compound of Formula (V).

In some embodiments, the compound of Formula (IV) is reacted with an excess amount of the dimethylamine in the presence base to provide the compound of Formula (V). In some embodiments, the compound of Formula (IV) is reacted with about 2 to about 6 molar equivalents, about 2 to about 4 molar equivalents, about 2 molar equivalents, about 3 molar equivalents, about 4 molar equivalents or about 5 molar equivalents or about 3.2 molar equivalents of the dimethylamine in the presence of the base to provide the compound of Formula (V). In some embodiments, the compound of Formula (IV) is reacted with about 3 to about 4 molar equivalents, or about 3.2 molar equivalents of the dimethylamine in the presence of the base to provide a compound of Formula (V).

In some embodiments, the compound of Formula (IV) is reacted with an excess amount of dimethylamine in the presence of the base at a temperature and a time for the compound of Formula (IV) to react with the dimethylamine in the presence of an excess amount (for example, about 2 to about 4 molar equivalents, about 2 molar equivalents, about 3 molar equivalents, about 4 molar equivalents or about 5 molar equivalents or about 3.2 molar equivalents) of base to provide the compound of Formula (V). In some embodiments, the base is an organic amine base that is a liquid at room temperature, such as triethylamine or pyridine. In some embodiments, the base is used as the solvent or solvent. In some embodiments, the base is triethylamine (TEA). In some embodiments, the base is TEA and the TEA is used as the solvent or co-solvent. In some embodiments, the dimethylamine and the base are used in equal amounts.

Accordingly, in some embodiments, the compound of Formula (IV) is reacted with an excess amount (for example, 3 to about 4 molar equivalents, or about 3.2 molar equivalents of the dimethylamine in the presence of an excess amount, (for example, about 3 to about 4 molar equivalents, or about 3.2 molar equivalents) of triethylamine to provide a compound of Formula (V).

In some embodiments, the compound of Formula (IV) is reacted with excess amount of the dimethylamine in the presence of the excess amount of base such as TEA to provide a compound of Formula (V) by combining the dimethylamine with the base to form a solution of the dimethylamine in the base and adding the solution to the compound of Formula (IV) at a temperature of about 0° C. to about 15° C., about 0° C. to about 10° C. or about 5° C. to about 10° C. or about 5° C. to form a reaction mixture and then allowing reaction mixture to warm to about 18° C. to about 25° C., about 20° C. to about 25° C. or room temperature and stirring the reaction mixture for about 2 hours to about 5 hours, about 3 hours to about 5 hour, about 3 hours to about 4 hours, or about 3 hours. Accordingly, in some embodiments, the compound of Formula (IV) is reacted with excess amount of the dimethylamine in the presence of the excess amount of base such as TEA to provide a compound of Formula (V) at a temperature of about 0° C. to about 10° C. or about 5° C. to about 10° C. or about 5° C. to form a reaction mixture, warming the reaction mixture to warm to room temperature and stirring the reaction mixture for about 3 hours to about 5 hour to provide the compound of Formula (V).

In some embodiments, the compound of Formula (IV) that is reacted with the dimethylamine to provide the compound of Formula (V) is crude or not purified or the compound of Formula (IV) is not isolated before reacting with the dimethylamine to provide a compound of Formula (V).

In some embodiments, the reducing agent to provide psilocin (II) from the compound of Formula (V) is any suitable reducing agent that reduces the ketone groups of the compound of Formula (V) to an alkane.

In some embodiments, the compound of Formula (V) is reduced with the reducing agent to provide psilocin (compound of Formula II) using any suitable conditions for reducing the compound of Formula (V) with the reducing agent to provide psilocin known in the art.

In some embodiments, the compound of Formula (V) is reduced with an excess amount (for example about 1.5 to about 3 molar equivalents or about 1.5 to about 2 molar equivalents, or about 2 molar equivalents) of the reducing agent in an inert solvent and at a temperature and a time for reducing the compound of Formula (V) with the reducing agent to provide psilocin. In some embodiments, the inert solvent is selected from ethers such as diethyl ether and tetrahydrofuran and hydrocarbon solvents such as toluene and mixtures thereof. In some embodiments, the inert solvent is selected from diethyl ether and toluene. In some embodiments, the inert solvent is tetrahydrofuran. As representative, non-limiting example of temperatures and reaction times, the reaction heated to the boiling point (reflux) is maintained at the boiling point for about 1 hour to about 6 hours, about 2 hours to about 6 hours, about 3 hours to about 5 hours, about 4 hours to about 5 hours, or about 4 hours.

In some embodiments, the suitable reducing agent for reducing the compound of Formula (V) is a metal hydride. In some embodiments, the metal hydride is selected from lithium borohydride, sodium borohydride and lithium aluminum hydride. In some embodiments, the metal hydride is lithium aluminum hydride. In some embodiment, the lithium aluminum hydride is provided as a solution in an inert solvent. Accordingly, in some embodiments, the lithium aluminum hydride is a lithium aluminum hydride solution. In some embodiments, the lithium aluminum hydride is a lithium aluminum hydride solution in THF. In some embodiments, the lithium aluminum hydride is a 1.0M lithium aluminum hydride solution in THF.

Accordingly, in some embodiments, compound of Formula (V) is reacted with about 1.5 to about 2 molar equivalents, or about 2 molar equivalents of lithium aluminum hydride in THF at the reflux temperature for about 3 hours to about 5 hours, about 4 hours to about 5 hours, or about 4 hours to provide the psilocin (II).

In some embodiments, psilocin is reacted with di-tert-butylphosphite in the presence of a base under modified Atherton-Todd reaction conditions to provide a compound of Formula (VI) In some embodiments, the psilocin is reacted with a slight excess (for example, about 1.1 to about 1.5 molar equivalents) of di-tert-butylphosphite in the presence of an excess (for example, about 1.5 to about 2.5 molar equivalents or about 2 molar equivalents) of base in an inert solvent at a temperature and for a time for reacting psilocin with the di-tert-butylphosphite to provide a compound of Formula (VI). In some embodiments, the inert solvent is selected from ethers such as diethyl ether and tetrahydrofuran, esters such as ethyl acetate, hydrocarbon solvents such as toluene, and halogenated solvents such as methylene chloride and carbon tetrachloride, and mixtures thereof. In some embodiments, the inert solvent is selected from tetrahydrofuran and carbon tetrachloride and mixtures thereof. In some embodiments, the inert solvent is a mixture of tetrahydrofuran and carbon tetrachloride. In some embodiments, the inert solvent is a 1:1 v/v mixture of tetrahydrofuran and carbon tetrachloride. In some embodiments, the base is a weak base. In some embodiments, the base is selected from (1,4-diazabicyclo[2.2.2]octane) (DABCO); 1,8-diazabicyclo[5.4.0]undec-7-ene (DBU); 4-dimethylaminopyridine (DMAP); alkylamines such as triethylamine and diethylamine; carbonates such as sodium carbonate and potassium carbonate; bicarbonates such as sodium bicarbonate and potassium bicarbonates; and hydroxides such as sodium hydroxide and potassium hydroxide, and combinations thereof. In some embodiments, the base is sodium hydroxide. In some embodiments, the base is sodium hydroxide in combination with DMAP. As representative, non-limiting example of temperatures and reaction times, in some embodiments, psilocin is reacted with di-tert-butylphosphite at about 18° C. to about 50° C. or about 20° C. to about 50° C. or room temperature for about 12 hours to about 20 hours, about 14 hours to about 18 hours or about 16 hours.

Accordingly, in some embodiments, the psilocin is reacted with a slight excess (for example, about 1.1 to about 1.5 molar equivalents) of di-tert-butylphosphite in the presence of an excess amount (for example, about 2 molar equivalents) of sodium hydroxide or a combination of excess amount (for example, about 2 molar equivalents) of sodium hydroxide in combination with about 0.1 molar equivalents of 4-dimethylaminopyridine (DMAP) in a mixture of tetrahydrofuran and carbon tetrachloride at room temperature for about 12 hours to about 20 hours, about 14 hours to about 18 hours or about 16 hours provide a compound of Formula VI.

In some embodiments, psilocin is reacted with chloro di-tert-butylphosphite to provide a compound of Formula (VI). In some embodiments, the chloro di-tert-butylphosphite is prepared in situ by reacting di tert butylphosphite with N-chloro succinimide (NCS) to provide the chloro di-tert-butyl phosphite. Accordingly, in some embodiments, the process comprises reacting psilocin with di-tert-butylphosphite and N-chloro succinimide (NCS) to provide a compound of Formula (VI). Therefore, in some embodiments, the step of reacting the psilocin with di-tert-butylphosphite and N-chloro succinimide to provide a compound of Formula (VI) comprises:

reacting di tert butylphosphite with N-chloro succinimide (NCS) to provide chloro di-tert-butyl phosphite; and reacting psilocin with chloro di-tert-butyl phosphite to provide a compound of Formula (VI).

In some embodiment, the di tert-butylphosphite is reacted with a slight excess (for example, 1.1 to about 2 molar equivalents, or about 1.2 molar equivalents) of NCS in an inert solvent such as THF at a temperature and a time to provide the chloro di-tert-butyl phosphite. As representative, non-limiting example of temperatures and reaction times, in some embodiments, tert butylphosphite is reacted with a slight excess (for example, about 1.1 to about 2 molar equivalents, or about 1.2 molar equivalents) of NCS at about 0° C. to about 15° C. or about 5° C. to about 10° C. or 5° C. for about 1 hour to about 4 hours, about 2 hours to about 4 hours, about 2 hours to about 3 hours or about 2 hours.

In some embodiments, reacting psilocin with the chloro di-tert-butyl phosphite to provide a compound of Formula (VI) comprises combining a slight excess (for example about 1.1 to about 2 molar equivalents or about 1.1 to about 1.5 molar equivalents) of chloro di-tert-butyl phosphite with psilocin at a temperature of about 0° C. to about 15° C. or about 5° C. to about 10° C. or 5° C. for about 2 hours to about 8 hours, about 2 hours to about 6 hours, about 3 hours to about 6 hours to provide a compound of Formula (VI).

In some embodiments, psilocybin (I) is prepared using any suitable conditions for hydrolyzing the compound of Formula (VI) to provide psilocybin known in the art.

In some embodiments, compound of Formula (VI) is hydrolyzed to provide psilocybin using an acid. Therefore, in some embodiments, the process comprises hydrolyzing the compound of Formula (VI) with an acid to provide psilocybin. In some embodiments, the acid is hydrochloric acid. In some embodiments, the compound of Formula (VI) is reacted with an excess amount of the acid (for example about 1.1 to about 1.5 molar equivalents) in a suitable solvent at a temperature and time for providing the psilocybin. As representative, non-limiting examples, the temperature and time for hydrolyzing the compound of Formula (VI) with the acid to provide psilocybin is about 18° C. to about 25° C. or about 20° C. to about 25° C. or room temperature for about 1 hour to about 4 hours, about 1 hours to about 3 hours, about 1.5 hours to about 2.5 hours, or about 2 hours.

Accordingly, in some embodiments, the compound of Formula (VI) is hydrolyzed with hydrochloric acid in acetone at room temperature for about 1 hours to about 3 hours or about 2 hours to provide psilocybin.

In some embodiments, the compound of Formula (VI) that is hydrolyzed to provide psilocybin is crude or not purified, or the compound of Formula (VI) is not isolated before being hydrolyzed to provide psilocybin.

In some embodiments, the compound of Formula (VI) is hydrolyzed with an acid in a suitable solvent at a temperature and time to form a reaction mixture comprising psilocybin and psilocybin is isolated from the reaction mixture. Accordingly, in some embodiments, the process comprises hydrolyzing the compound of Formula (VI) to provide a reaction mixture comprising psilocybin; and isolating psilocybin.

In some embodiments, psilocybin is isolated from the reaction mixture using any suitable conditions for isolating a product such as psilocybin from a reaction mixture known in the art.

In some embodiments, the step of isolating psilocybin comprises:

adjusting the pH of the reaction mixture to a pH of 6 to 7;

extracting impurities from the reaction mixture with a suitable first solvent:

extracting psilocybin from the reaction mixture with a suitable second solvent to provide a psilocybin solution;

concentrating the psilocybin solution and crystallizing psilocybin from the psilocybin solution: and separating psilocybin from the crude psilocybin solution to provide psilocybin.

In some embodiments, the pH of the reaction mixture is adjusted using base.

In some embodiments, the suitable first solvent is isopropyl alcohol, 2-methyl tetrahydrofuran or water, mixtures thereof.

In some embodiments, the suitable second solvent is water or heptane.

In some embodiments, the first solvent is isopropyl alcohol and the second solvent is water. In some embodiments, the first solvent is 2-methyl tetrahydrofuran and the second solvent is heptane. In some embodiments, the first solvent is water and the second solvent is heptane.

In some embodiments, the step of concentrating of the psilocybin solution is by distillation or rotoevapouration.

In some embodiments, the separating psilocybin from the psilocybin solution is by filtration. In some embodiments, the separating psilocybin from the psilocybin solution is by filtration using filter aids. In some embodiments, the filters aids are diatomaceous earth (DE), perlite, cellulose and combinations thereof.

In some embodiments, the process further comprises purifying the psilocybin. In some embodiments, psilocybin is purified using any suitable conditions for purifying a product such as psilocybin known in the art.

In some embodiments, purifying psilocybin comprises dissolving psilocybin in water to provide an aqueous psilocybin solution;

neutralizing the aqueous psilocybin solution;

extracting psilocybin from the aqueous psilocybin solution with a suitable solvent to form a pure psilocybin solution;

concentrating the pure psilocybin solution and crystallizing pure psilocybin from the pure psilocybin solution: and separating the pure psilocybin from the pure psilocybin solution to provide pure psilocybin.

In some embodiments, the neutralizing the aqueous psilocybin solution is with an acid.

In some embodiments, the step of concentrating of the pure psilocybin solution is by distillation or rotoevapouration.

In some embodiments, the separating the pure psilocybin from the pure psilocybin solution is by filtration.

In some embodiments, the process of the application provides intermediates including psilocin in a desired polymorphic form.

In some embodiments, the step of crystallizing pure psilocybin provides psilocybin in a desired polymorphic form.

In some embodiments, the crystallizing pure psilocybin provides pure psilocybin, of consistent polymorphic form, for administration to human subjects.

In some embodiments, the process provides intermediates, including but not limited to psilocin, different polymorphic forms of psilocybin, and prodrugs and analogs thereof and their formulation for use in medicine.

In an exemplary embodiment of the processes of the application, the present application includes a process for preparing psilocybin (compound of Formula I):

(I)

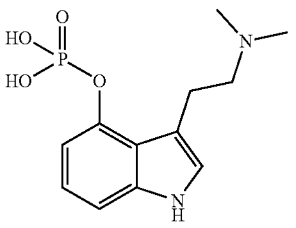

the process comprising:

reacting unprotected 4-hydroxyindole (compound of Formula III):

(III)

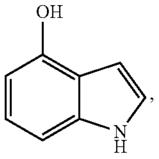

with an excess amount of oxalyl chloride to provide a compound of Formula (IV):

(IV)

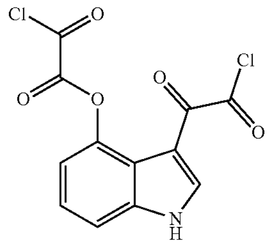

reacting the compound of Formula (IV) with an excess amount of dimethylamine hydrochloride ($HN(CH_3)_2 \cdot HCl$) in the presence of base to provide a compound of Formula (V):

(V)

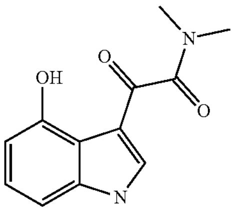

reducing the compound of Formula (V) with a reducing reagent to provide psilocin (compound of Formula II);

(II)

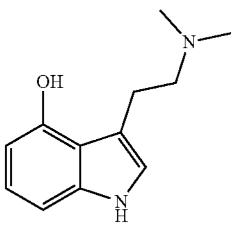

reacting psilocin with di-tert-butylphosphite,

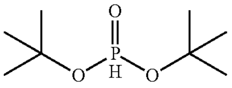

in the presence of a base to provide a compound of Formula VI:

(VI)

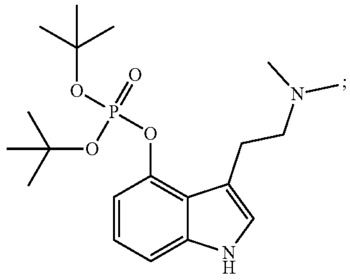

and hydrolyzing the compound of Formula VI with an acid to provide psilocybin (compound of Formula I).

In some embodiments, the unprotected 4-hydroxyindole (compound of Formula III) is reacted with oxalyl chloride in diethyl ether to provide a compound of Formula (IV).

In some embodiments, the unprotected 4-hydroxyindole (compound of Formula III) is reacted with oxalyl chloride in methyl tert-butyl ether (MTBE) to provide a compound of Formula (IV).

In some embodiments, the compound of Formula IV is not isolated prior to reacting with an excess amount of dimethylamine hydrochloride in the presence of a base.

In some embodiments, the compound of Formula (IV) is reacted with an excess amount of dimethylamine hydrochloride ($HN(CH_3)_2 \cdot HCl$) in the presence of pyridine to provide a compound of Formula VI.

In some embodiments, the psilocin is reacted with di-tert-butylphosphite in the presence of sodium hydroxide or a combination of sodium hydroxide in combination 4-dimethylaminopyridine (DMAP) in a mixture of tetrahydrofuran and carbon tetrachloride to provide a compound of Formula (VI).

In some embodiments, the compound of Formula VI is not isolated prior to hydrolyzing with an acid to provide psilocybin.

In an exemplary embodiment of the processes of the application, the present application includes a process for preparing psilocybin (compound of Formula I):

(I)

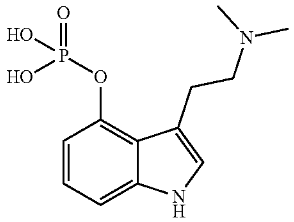

the process comprising:

reacting unprotected 4-hydroxyindole (compound of Formula III):

(III)

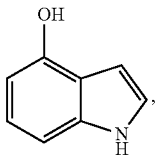

with an excess amount of oxalyl chloride to provide a compound of Formula (IV):

(IV)

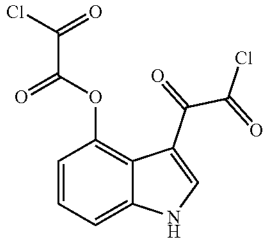

reacting the compound of Formula (IV) with an excess amount of dimethylamine to provide a compound of Formula (V):

(V)

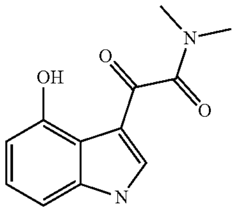

reducing the compound of Formula (V) with a reducing reagent to provide psilocin (compound of Formula II);

(II)

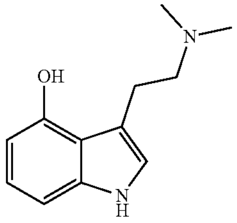

reacting psilocin with chloro di-tert-butylphosphite,

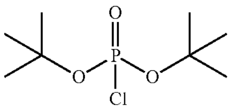

to provide a compound of Formula VI:

(VI)

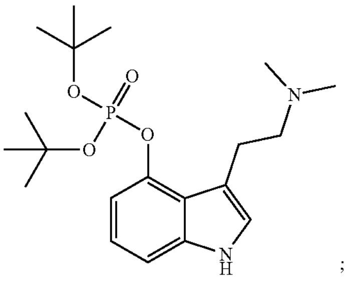

;

and hydrolyzing the compound of Formula VI with an acid to provide psilocybin (compound of Formula I).

In some embodiment, the chloro di-tert-butylphosphite is prepared in situ by reacting di tert butylphosphite with N-chloro succinimide (NCS) to provide the chloro di-tert-butyl phosphite. Accordingly, in some embodiments, the process comprises reacting psilocin with di-tert-butylphosphite and N-chloro succinimide (NCS) to provide a compound of Formula (VI). Therefore, in an exemplary embodiment of the processes of the application, the present application includes a process for preparing psilocybin (compound of Formula I):

(I)

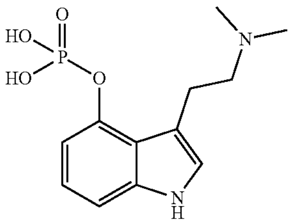

the process comprising:

reacting unprotected 4-hydroxyindole (compound of Formula III):

(III)

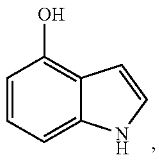

, with an excess amount of oxalyl chloride to provide a compound of Formula (IV):

(IV)

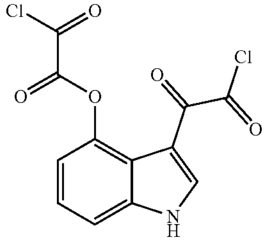

reacting the compound of Formula (IV) with an excess amount of dimethylamine to provide a compound of Formula (V):

(V)

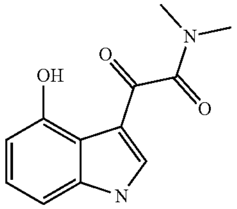

reducing the compound of Formula (V) with a reducing reagent to provide psilocin (compound of Formula II);

(II)

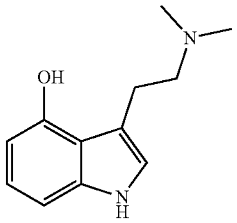

reacting psilocin with di-tert-butylphosphite,

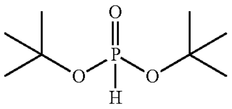

and N-chloro succinimide (NCS) to provide a compound of Formula VI:

(VI)

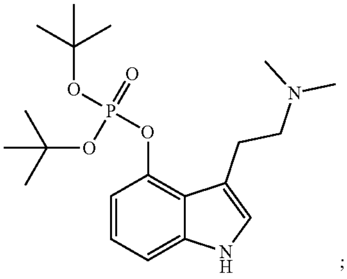

;

and hydrolyzing the compound of Formula VI with an acid to provide psilocybin (compound of Formula I).

In some embodiments, the unprotected 4-hydroxyindole (compound of Formula III) is reacted with oxalyl chloride in methyl tert-butyl ether (MTBE) to provide a compound of Formula (IV).

In some embodiments, the compound of Formula IV is not isolated prior to reacting with an excess amount of dimethylamine.

In some embodiments, the compound of Formula (IV) is reacted with an excess amount of dimethylamine in the presence of a base to provide a compound of Formula VI. In some embodiments, the compound of Formula (IV) is reacted with an excess amount of dimethylamine in the presence of triethylamine to provide a compound of Formula VI. In some embodiments, the triethylamine is the solvent.

In some embodiments, the compound of Formula VI is not isolated prior to hydrolyzing with an acid to provide psilocybin.

In an exemplary embodiment of the processes of the application, the present application comprises a process for preparing psilocybin and its active metabolite psilocin of the Formula (I) and Formula (II) respectively, Formula (I)

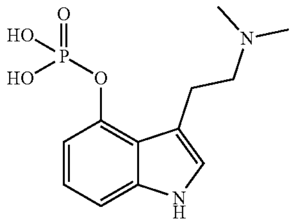

Formula (II)

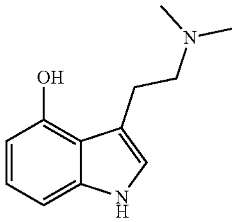

comprising:

reacting unprotected 4-hydroxyindole of Formula (III):

Formula (III)

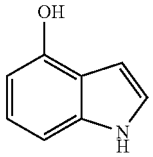

with about 3 equivalents of oxalyl chloride at a temperature of about 0° C. for about 16 hours, to provide a compound of Formula (IV):

(IV)

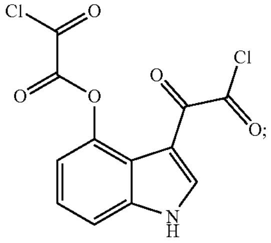

reacting the crude compound of Formula (IV) with an excess of dimethylamine hydrochloride in the presence of pyridine in diethyl-ether, at about room temperature for about 30 minutes, to provide a compound of Formula (V):

(V)

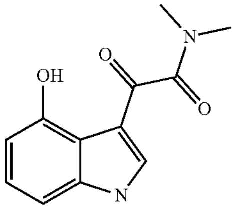

reducing the compound of Formula (V) with an excess of lithium aluminum hydride in a 1.0 M pure psilocybin solution in tetrahydrofuran (THF) at reflux temperature for about 4 hours, to provide psilocin, compound of Formula (II);

reacting psilocin with about 1.1 equivalents of di-tert-butylphosphite in the presence of a weak base in carbon tetrachloride ($CCl_4$) and tetrahydrofuran (THF), in a ratio of 1:1 v/v $CCl_4$ to THF, for about 6 hours at about room temperature to provide di-tert-butyl compound of Formula (VI):

(VI)

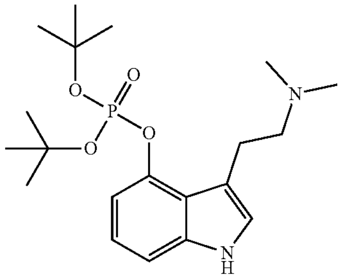

hydrolyzing the compound of Formula (VI) with about 6M hydrogen chloride in acetone to form a reaction mixture and stirring the reaction mixture at room temperature for 2 about hours;

neutralizing the reaction mixture to a pH 6-7 with an base;

extracting liberated impurities from the reaction mixture with a first suitable organic solvent;

extracting crude psilocybin from the reaction mixture with a suitable second organic solvent to form a psilocybin solution;

concentrating the psilocybin solution and crystallizing crude psilocybin;

isolating the crude psilocybin by filtration;

dissolving the crude psilocybin in water to form an aqueous psilocybin solution and neutralizing the aqueous psilocybin solution with a weak acid;

extracting pure psilocybin base from the aqueous psilocybin solution with a suitable solvent to form a pure psilocybin solution;

concentrating the pure psilocybin solution and crystallizing pure psilocybin from the pure psilocybin solution; and isolating the pure psilocybin from the pure psilocybin solution by filtration.

In some embodiments, the present application also includes a new process synthetic route for the preparation of psilocybin and its active metabolite psilocin of the Formula (I) and Formula (II) respectively, Formula (I)

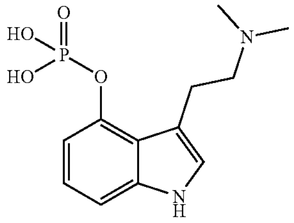

Formula (II)

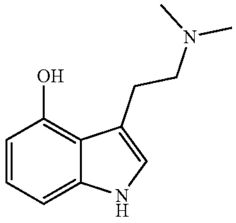

the process comprising:

(i) reacting unprotected 4-hydroxyindole of formula (III):

Formula (III)

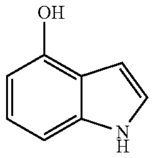

(ii) addition of 3 equivalents of oxalyl chloride to an organic solvent solution of unprotected 4-hydroxyindole, at a temperature of 0° C. for 16 hours, to yield 3-(2-chloro-2-oxoacetyl)-1H-indol-4-yl 2-chloro-2-oxoacetate of Formula (IV):

Formula (IV)

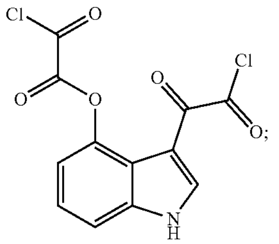

(iii) addition of excess of dimethylamine hydrochloride to a diethyl-ether/pyridine solution of crude 3-(2-chloro-2-oxoacetyl)-1H-indol-4-yl 2-chloro-2-oxoacetate of Formula (IV), at room temperature for 30 minutes, to provide exclusively 2-(4-hydroxy-1H-indol-3-yl)-N,N-dimethyl-2-oxoacetamide of Formula V:

Formula (V)

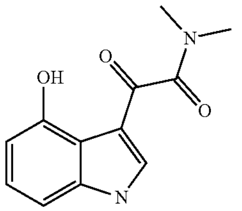

(iv) addition of excess of lithium aluminum hydride solution 1.0 M in tetrahydrofuran (THF) to a THF solution of 2-(4-hydroxy-1H-indol-3-yl)-N,N-dimethyl-2-oxoacetamide of Formula (V), under THF reflux for 4 hours, to provide 3-(2-(dimethylamino) ethyl)-1H-indol-4-ol (psilocin) of Formula II, addition of 1.1 equivalents of di-tert-butylphosphite to a weak base in a solution of carbon tetrachloride (0014) and tetrahydrofuran (THF), 1:1 v/v, for 6 hours at room temperature to yield crude di-tert-butyl (3-(2-(dimethylamino)ethyl)-1H-indol-4-yl) phosphate of Formula (VI):

Formula (VI)

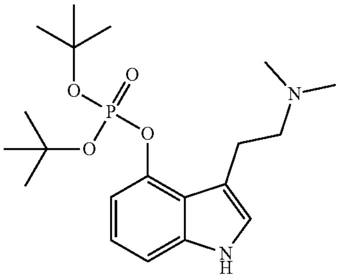

(vii) addition of 6M hydrogen chloride in acetone to crude di-tert-butyl (3-(2-(dimethylamino)ethyl)-1H-indol-4-yl) phosphate;

(viii) stirring of reaction mass at room temperature and maintenance of reaction mass at room temperature for 2 hours;

(ix) neutralization to pH 6-7 with a base;

(x) removal of liberated impurities from the reaction mass by extraction into an organic solvent;

(xi) extraction of crude psilocybin base into an organic solvent;

(xii) distillation of solvent and formation of crude psilocybin in an organic solvent;

(xiii) isolation of crude psilocybin solution by filtration;

(xiv) dissolution of crude psilocybin in water medium and neutralization with a weak acid;

(xv) extraction of pure psilocybin base into a solvent;

(xvi) partial distillation of solvent and crystallization of psilocybin base from same solvent; and (xvii) isolation of pure psilocybin base by filtration.

In some embodiments, the temperature of reaction mass in step (i) is 0-10° C., more preferably 0-5° C.

In some embodiments, the organic solvent in step (i) is diethyl-ether. In some embodiments, the organic solvent in step (i) is methyl tert-butyl ether.

In some embodiments, the excess of dimethylamine hydrochloride used in step (ii) is 3 equivalents, preferably 5 equivalents, In some embodiments, the organic solvent used in steps (i), (ii), or (iii) is selected from inert solvent such as tetradrofuran, hydrocarbon solvents such as toluene, preferably toluene.

In some embodiments, the excess of lithium aluminum used in step (iii) is 2 equivalents, In some embodiments, the weak base used in step (iv) is selected from (1,4-diazabicyclo[2.2.2]octane) (DABCO), 1,8-diazabicyclo[5.4.0]undec-7-ene (DBU) or alkylamines such as triethylamine and diethylamine, carbonate or bicarbonate, preferably sodium or potassium carbonate or sodium or potassium hydroxide, preferably sodium hydroxide, preferably sodium hydroxide.

In some embodiments, the organic solvent used for hydrolysis in step (iv) is selected from ketones, preferably acetone, In some embodiments, the solvent used in step (iv) for purification is selected from alcohols like methanol, ethanol, isopropanol, ketones like acetone, methyl ethyl nitriles like acetonitrile with or without a combination of water, In some embodiments, the purification provides a method of crystallising psilocybin in a desired polymorphic form.

In some embodiments, the crystallization provides chemically pure psilocybin, of consistent polymorphic form, for administration to human subjects.

In some embodiments, the purity of crude psilocybin (e.g. psilocybin before the step of purifying) obtained by the process of present application starting from 4-hydroxyindole is more than about 95% wherein any one impurity is less than about 1.5%. In some embodiments, the purity of crude psilocybin (e.g. psilocybin before the step of purifying) obtained by the process of present application is more than about 90%, more than about 91%, more than about 92%, more than about 93%, more than about 94%, more than about 95%, more than about 96%, more than about 97% or more than about 98%, wherein any one impurity is less than about 1.5%.

In some embodiments, the crude psilocybin obtained by the process comprises less than about 5% psilocin, less than about 4% psilocin, less than about 3% psilocin, less than about 2% psilocin or less than about 1% psilocin.

In some embodiments, the purity of pure psilocybin obtained by the process of the application starting from 4-hydroxyindole is more than about 98.0% wherein any one impurity is less than about 0.2%, or about 0.15% and the purity of psilocybin is more than about 98.0%, or more than about 99% with the total impurities in less than about 0.15% or about 0.10%.

In some embodiments, the pure psilocybin obtained by the process comprises less than about 1% psilocin.

In some embodiments, the present application also includes HPLC methods for the analysis and assay of psilocybin, psilocin and intermediate compounds of Formula (III), (IV), (V) and (VI). In some embodiments, the present application includes an HPLC method for assaying psilocybin comprising:

dissolving psilocybin sample in acetonitrile:water 0.1% $H_3PO_4$ (1:1) diluent;

injecting the sample solution (ca. 10 ul) onto a 100 mm×4 mm, 3 um RP-18 HPLC column;

eluting the sample from the column at 1 ml/min. using a mixture of acetonitrile (28 vol-%) and ammonium-format buffer (72 vol-%, 0.005 M. pH-4) as eluent; and measuring the psilocybin content of the relevant sample at 245 nm wavelength with a UV detector.

A person skilled in the art would appreciate that further manipulation of the substituent groups using known chemistry can be performed on the intermediates and final compounds in the Schemes above to provide alternative compounds of the application.

Psilocybin and psilocin can be employed in the form of pharmaceutically acceptable salts. Those skilled in the art will recognize those instances in which the psilocybin and psilocin of the present invention may form salts. Examples of such psilocybin and psilocin are described herein by reference to possible salts. Such reference is for illustration only. Pharmaceutically acceptable salts can be used with psilocybin and psilocin for treating subjects. Non pharmaceutical salts may, however, be useful in the preparation of psilocybin and psilocin intermediates. The term "pharmaceutically acceptable salt" refers to a salt (including an inner salt such as a zwitterion) that possesses effectiveness similar to the parent compound and that is not biologically or otherwise undesirable (e.g, is neither toxic nor otherwise deleterious to the recipient thereof). Thus, an embodiment of the invention provides pharmaceutically acceptable salts of psilocybin and/or psilocin. The term "salt(s)", as employed herein, denotes any of the following: acidic salts formed with inorganic and/or organic acids, as well as basic salts formed with inorganic and/or organic bases.

Salts of psilocybin and/or psilocin may be formed by methods known to those of ordinary skill in the art, for example, by reacting psilocybin and/or psilocin with an amount of acid or base, such as an equivalent amount, in a medium such as one in which the salt precipitates or in aqueous medium followed by lyophilization.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. As both compounds (I) and (II) have an amine group, acid addition salt can be formed. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt. Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), and Handbook of Pharmaceutical Salts. Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

All such acid salts are intended to be pharmaceutically acceptable salts within the scope of the invention and all acid and base salts are considered equivalent to the free forms of the corresponding compounds for purposes of the invention. In addition, psilocybin and psilocin of the invention contains both acidic and basic moieties, and therefore it is understood that psilocybin of the present invention may exist in zwitterionic form, having both anionic and cationic centers within the same psilocybin and a net neutral charge. Such zwitterions are included within the invention.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Isotopically-enriched compounds of the application and pharmaceutically acceptable salts, solvates and/or prodrug thereof, can be prepared without undue experimentation by conventional techniques well known to those skilled in the art or by processes analogous to those described in the Schemes and Examples herein using suitable isotopically-enriched reagents and/or intermediates.

Throughout the processes described herein it is to be understood that, where appropriate, suitable protecting groups will be added to and subsequently removed from, the various reactants and intermediates in a manner that will be readily understood by one skilled in the art. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities and ways to circumvent them by carrying out appropriate transformations and synthetic steps in a suitable order, will be readily understood to one skilled in the art. Examples of transformations are given herein and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

III. Compounds and Compositions

The present application provides processes for the preparation of psilocybin and psilocin. Accordingly, the present application includes psilocybin prepared by the processes of the application described above. The present application also includes psilocin prepared by the processes of the application described above.

The present application also includes a compound of Formula IV

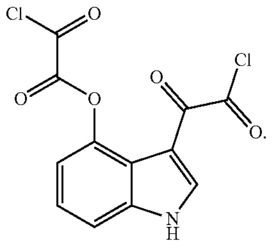

(IV)

The present application also includes a compound of Formula VI

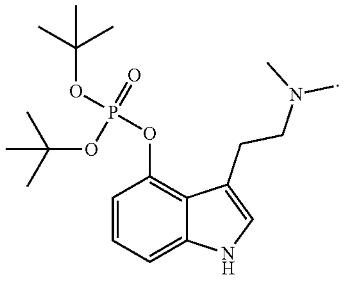

(IV)

In some embodiments, psilocybin, psilocin and their intermediates or pharmaceutically acceptable salts thereof, are as illustrated below:

| Compound ID # | Chemical Structure | IUPAC Name | Molecular Weight/ Chemical Formula |
|---|---|---|---|
| (I) | 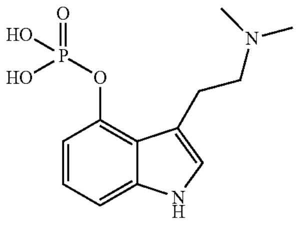 [SMILES: CN(C)CCc1c[nH]c2cccc(OP(=O)(O)O)c12] | 3-(2-(dimethyl-amino)ethyl)-1H-indol-4-yl dihydrogen phosphate | $C_{12}H_{17}N_2O_4P$ 284.252 |
| (II) | 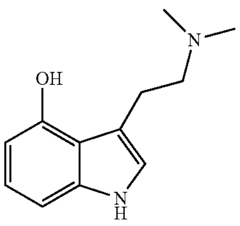 | 3-(2-(dimethyl-amino)ethyl)-1H-indol-4-ol | $C_{12}H_{16}N_2O$ 204.27 |

-continued

| Compound ID # | Chemical Structure | IUPAC Name | Molecular Weight/ Chemical Formula |
|---|---|---|---|
| (IV) | 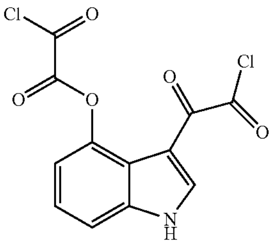 [SMILES: O=C(Cl)C(=O)Oc1cccc2[nH]cc(C(=O)C(=O)Cl)c12] | 3-(2-chloro-2-oxoacetyl)-1H-indol-4-yl 2-chloro-2-oxoacetate | $C_{12}H_5Cl_2NO_5$: 314.07 |
| (V) | 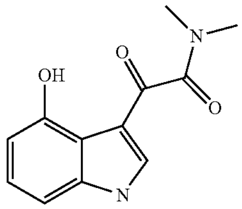 [SMILES: CN(C)C(=O)C(=O)c1c[nH]c2cccc(O)c12] | 2-(4-hydroxy-1H-indol-3-yl)-N,N-dimethyl-2-oxoacetamide | $C_{12}H_{12}N_2O_3$: 232.24 |
| (VI) | 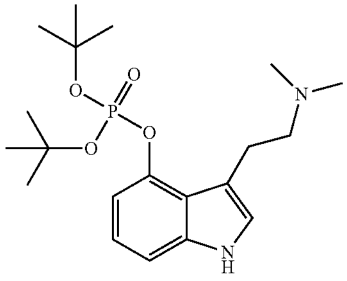 [SMILES: CN(C)CCc1c[nH]c2cccc(OP(=O)(OC(C)(C)C)OC(C)(C)C)c12] | di-tert-butyl (3-(2-(dimethylamino)ethyl)-1H-indol-4-yl)phosphate | $C_{20}H_{33}N_2O_4P$ 396.47 |

Psilocybin and psilocin can be employed in the form of pharmaceutically acceptable salts as described above.

and/or psilocin may further exist in varying polymorphic forms and it is contemplated that any polymorphs, or mixtures thereof, which form are included within the scope of the present application.

Psilocybin and/or psilocin may further be radiolabeled and accordingly all radiolabeled versions of the Psilocybin and/or psilocin are included within the scope of the present application. Psilocybin and/or psilocin also include those in which one or more radioactive atoms are incorporated within their structure.

Psilocybin and/or psilocin of the present application are suitably formulated in a conventional manner into compositions using one or more carriers. Psilocybin and psilocin of the present application is suitably formulated into pharmaceutical compositions for administration to subjects in a biologically compatible form suitable for administration in vivo. In embodiments of the application the pharmaceutical compositions are used in the treatment of any of the diseases, disorders or conditions such as mental health disorders such as major depressive disorder, anxiety and addiction disorders, among others CNS disorders.

EXAMPLES

The following non-limiting examples are illustrative of the present application.

General Methods

All starting materials used herein were commercially available or earlier described in the literature. The $^1H$ and $^{13}C$ NMR spectra were recorded either on Bruker 300, Bruker DPX400 or Varian +400 spectrometers operating at 300, 400 and 400 MHz for $^1H$ NMR respectively, using TMS or the residual solvent signal as an internal reference, in deuterated chloroform as solvent unless otherwise indicated. All reported chemical shifts are in ppm on the delta-scale, and the fine splitting of the signals as appearing in the recordings is generally indicated, for example as s: singlet, br s: broad singlet, d: doublet, t: triplet, q: quartet, m: multiplet. Unless otherwise indicated, in the tables below, $^1H$ NMR data was obtained at 400 MHz, using $CDCl_3$ as the solvent.

Purification of products was carried out using Chem Elut Extraction Columns (Varian, cat #1219-8002), Mega BE-SI (Bond Elut Silica) SPE Columns (Varian, cat #12256018; 12256026; 12256034) or by flash chromatography in silica-filled glass columns.

Example 1: Exemplary Preparation of Psilocin (II) and Psilocybin (I)

Scheme 5

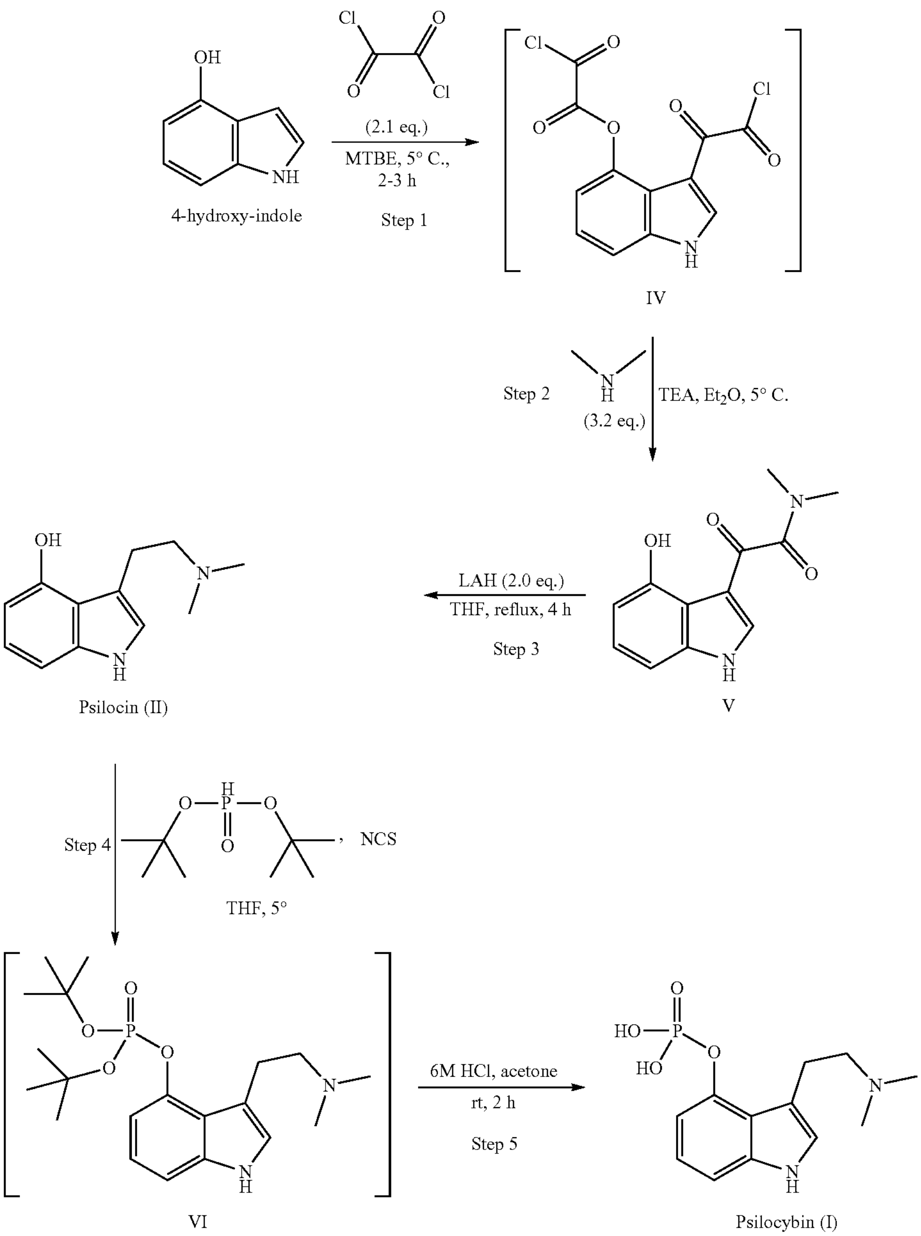

4-hydroxy-indole

IV

V

Psilocin (II)

VI

Psilocybin (I)

Step 1: 3-(2-chloro-2-oxoacetyl)-1H-indol-4-yl 2-chloro-2-oxoacetate (Compound of Formula IV)

Oxalyl chloride (2.1 eq) was dissolved in 2V of methyl tert-butyl ether (MTBE), and cooled to 5° C. Unprotected 4-hydroxyindole (1 eq) was dissolved in 8V of MTBE, and slowly added to the cooled oxalyl chloride solution via dropping column. Reaction mixture was allowed to stir for 2-3 hours. In-process control (IPC) sample taken by removing 0.05 ml and diluting in 20 ml of HPLC grade acetonitrile. IPC pass at <5% 4-hydroxyindole (See HPLC, FIG. 1). Reaction mixture telescoped into Step 2.

Step 2: 2-(4-hydroxy-1H-indol-3-yl)-N,N-dimethyl-2-oxoacetamide (Compound of Formula V)

A solution of 3.2 eq dimethylamine (2.0M in THF), and 3.2 eq triethylamine was placed into a dropping column. Dimethyl amine solution was added slowly to the crude Step 1 reaction mixture, stirring at 5° C. Controlling for exotherm (keeping solution <10° C.). Reaction mixture was warmed to 20° C., and allowed to stir for 3 hours. IPC pass at <5% Step 1 intermediate remaining. n-heptane (13.3V) added slowly, cooled to 5° C. and stirred for ~1 hour. The slurry was filtered, and all retained solids were re-dissolved in 4V 2-MeTHF relative to wet cake mass. 2-MeTHF/product solution was filtered to remove salts, then concentrated to 5V. The organic layer was washed with 5V 5% brine to purge tetramethyloxalamide impurity, followed by 5V HP water. The organic layer was then dried with Sodium sulfate. n-heptane (10 V) was added slowly to precipitate product. The product was filtered and dried in vacuum oven to produce intermediate (V).

Figure 2:
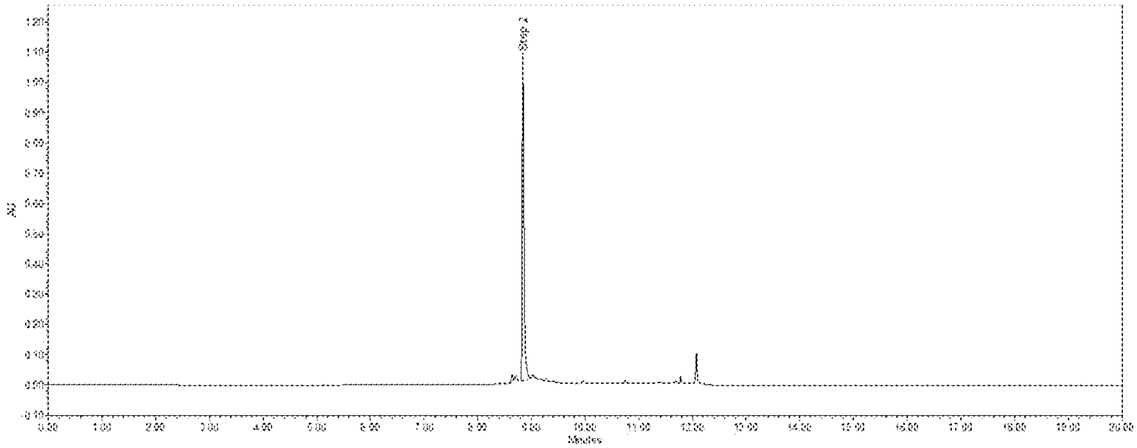
FIG. 2 shows an HPLC chromatogram of the compound of Formula V.
Figure 3:
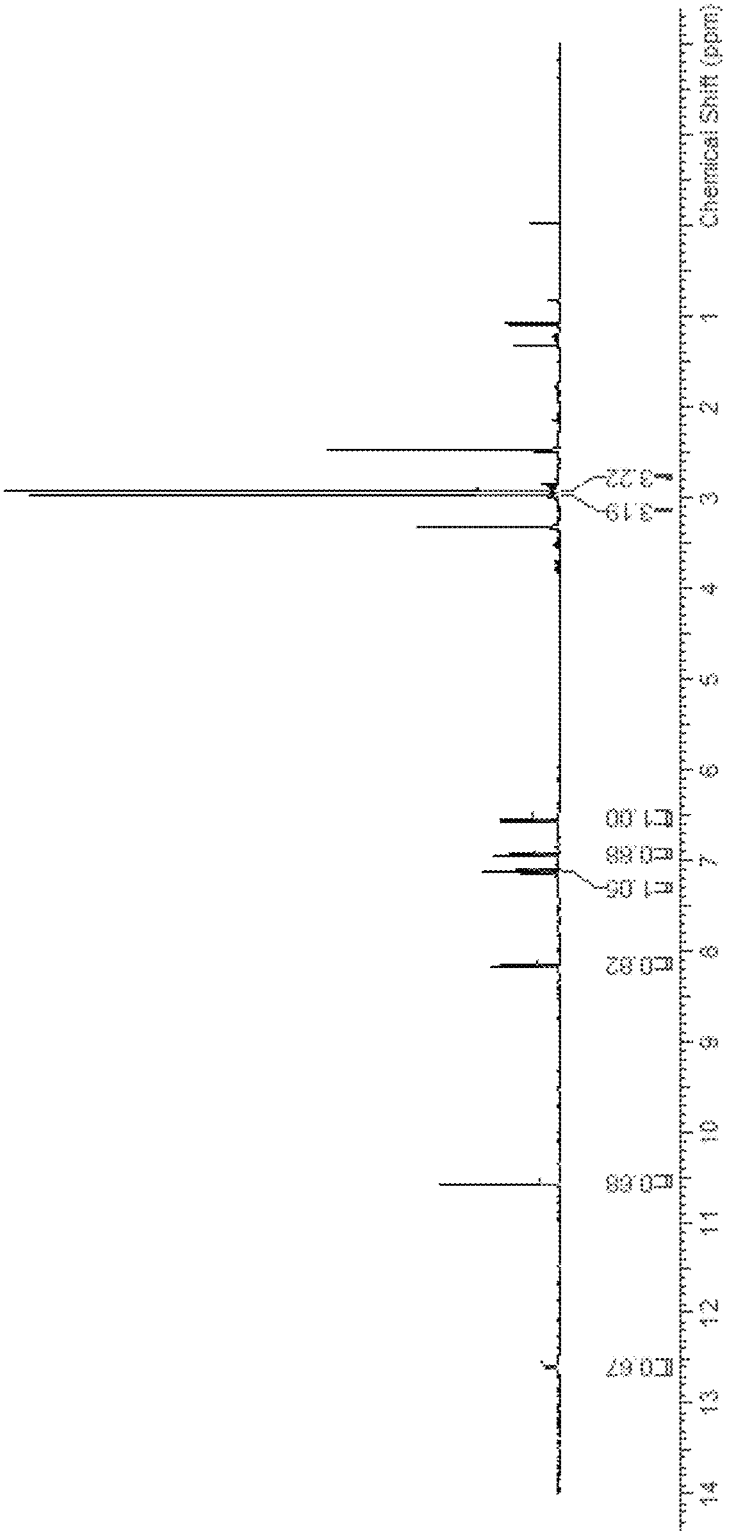
FIG. 3 shows a $^1$H NMR spectrum of the compound of Formula V.

HPLC: See FIG. 2, $^1$H NMR (300 MHz, DMSO-D6): See FIG. 3

Step 3: 3-(2-(dimethylamino)ethyl)-1H-indol-4-ol (Psilocin, Compound of Formula II)

2 equivalents of lithium aluminum hydride ($LiAlH_4$) solution 1.0 M in tetrahydrofuran (THF) was added to a THF solution of 2-(4-hydroxy-1H-indol-3-yl)-N,N-dimethyl-2-oxoacetamide (V) under THF reflux for 4 hours, to provide 3-(2-(dimethylamino)ethyl)-1H-indol-4-ol (psilocin).

Figure 4:
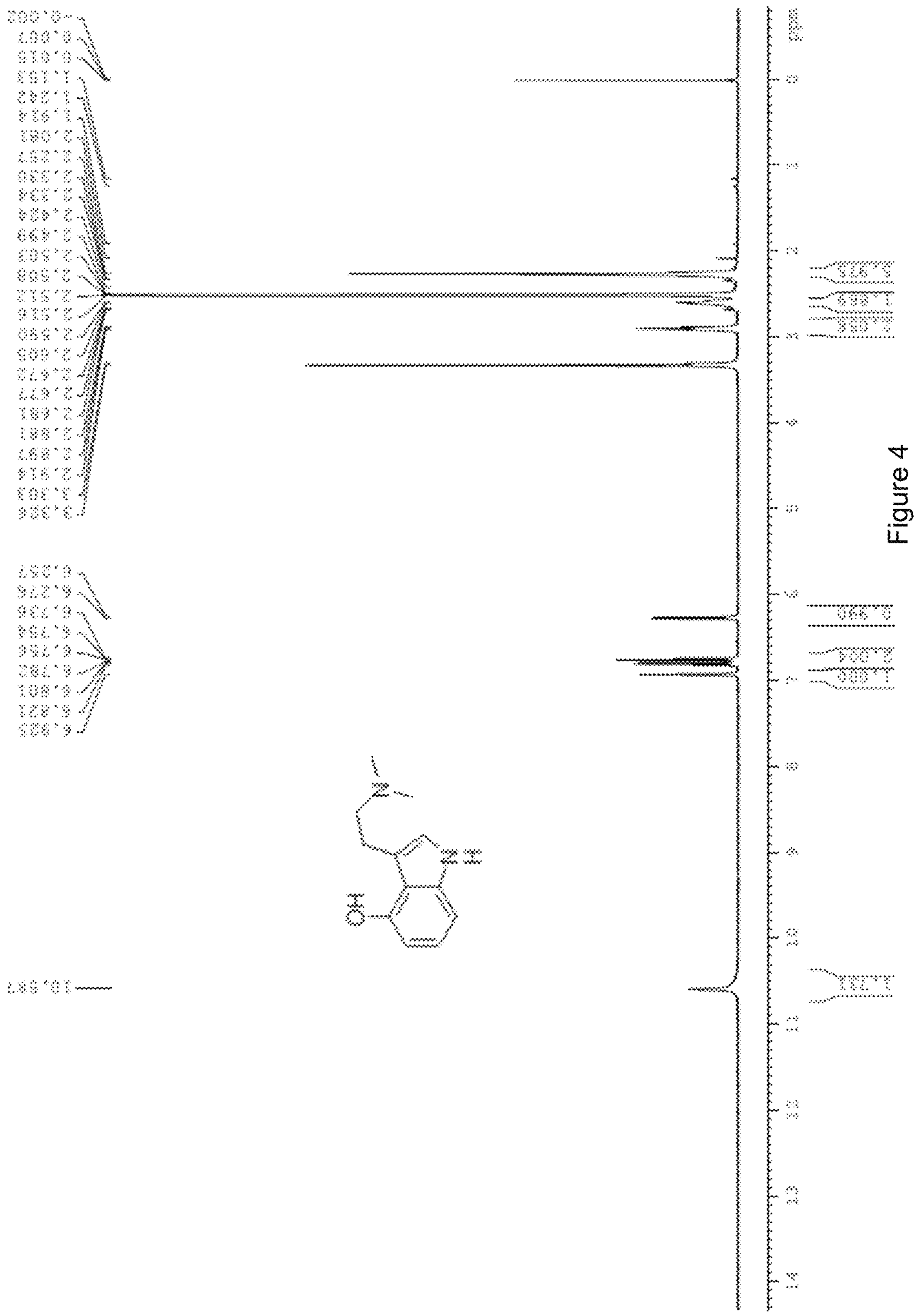
FIG. 4 shows a $^1$H NMR spectrum of psilocin (compound of Formula II).

$^1$H NMR (300 MHz, DMSO-D6): see FIG. 4

Step 4: di-tert-butyl (3-(2-(dimethylamino)ethyl)-1H-indol-4-yl) phosphate (Compound of Formula VI)

1 g of di-tert-butyl phosphite was dissolved in 5V of THF, and added to 1.2 eq of N-chlorosuccinimide (NCS)/5V THF at 5° C. to generate chloro di-tert-butyl phosphite in situ.

Figure 5:
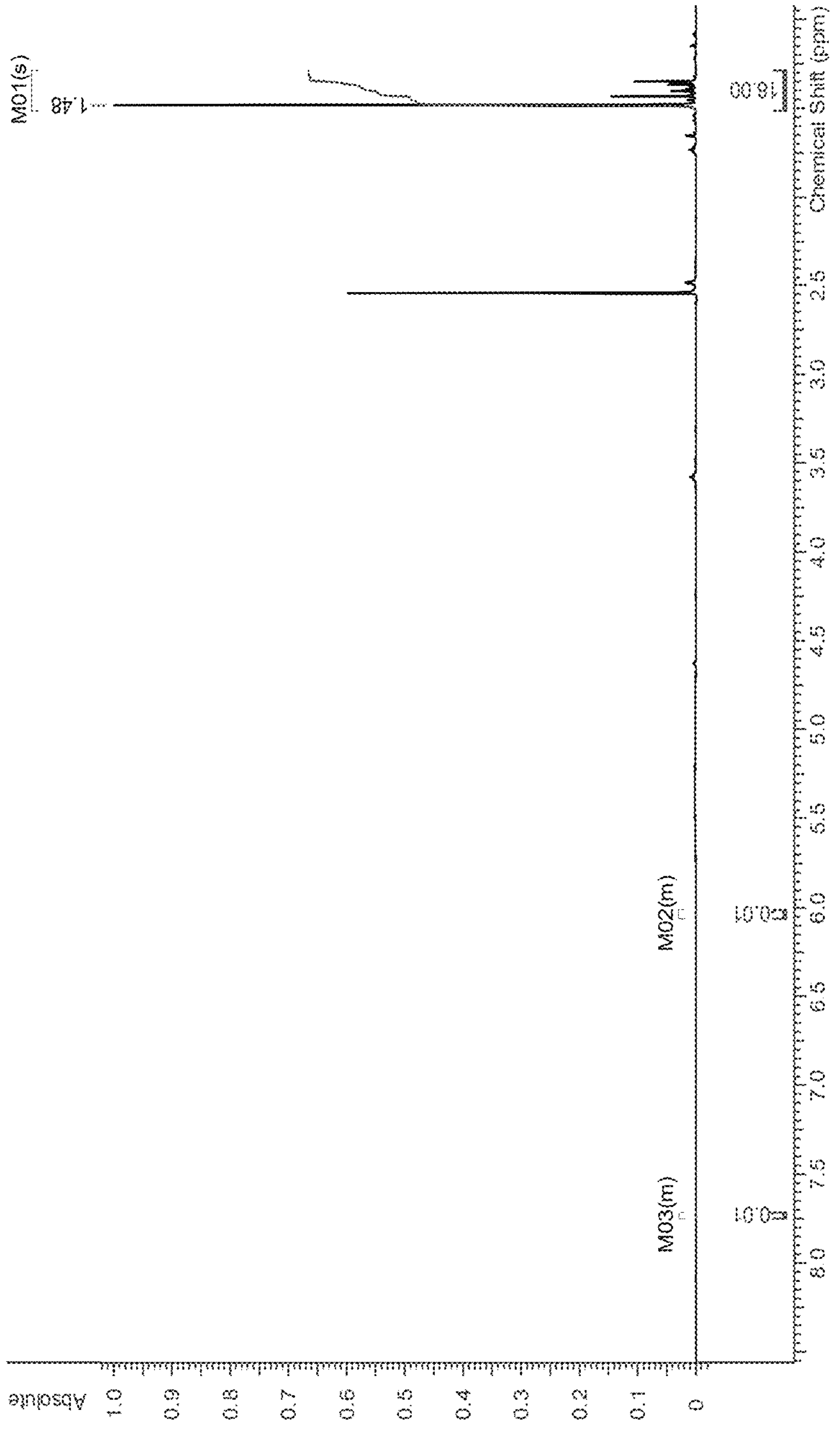
FIG. 5 shows a $^1$H NMR spectrum of chloro di-tert-butylphosphite.

$^1$H NMR (300 MHz, $CDCl_3$), See FIG. 5

Psilocin is treated with lithium diisopropylamide and a catalytic amount of DMAP in THF at 0° C. followed by the dropwise addition of the crude chloro di-tert-butyl phosphite to provide the corresponding di-tert-butyl (3-(2-(dimethylamino)ethyl)-1H-indol-4-yl) phosphate.

Step 5: Psilocybin 6M hydrogen chloride (HCl) in acetone is added to the crude di-tert-butyl (3-(2-(dimethylamino)ethyl)-1H-indol-4-yl) phosphate; (ii) the reaction mass is stirred at room temperature and maintained at room temperature for 2 hours; (iii) the reaction mass is then neutralized to pH 6-7 with a base; (iv) liberated impurities are removed from the reaction mass by extraction into an organic solvent; (v) crude psilocybin base is extracted into an organic solvent; (vi) solvent is distilled and crude psilocybin in an organic solvent is provided; crude psilocybin solution is isolated by filtration; (vii) crude psilocybin is dissolved in water medium and neutralized with a weak acid; (viii) pure psilocybin base is extracted into a solvent; (ix) the solvent is partially distilled and psilocybin is crystallized from same solvent; and (x) pure psilocybin is isolated by filtration.

Example 2: Exemplary Preparation of Psilocin (II) and Psilocybin (I)

Scheme 6

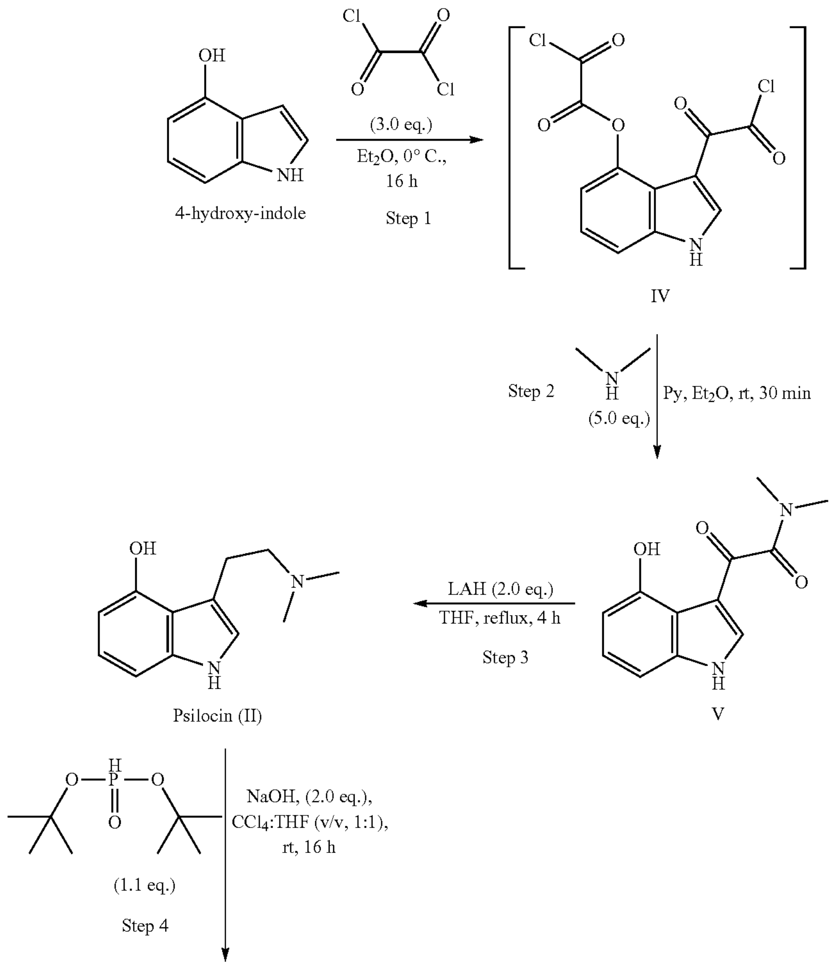

4-hydroxy-indole

IV

V

Psilocin (II)

-continued

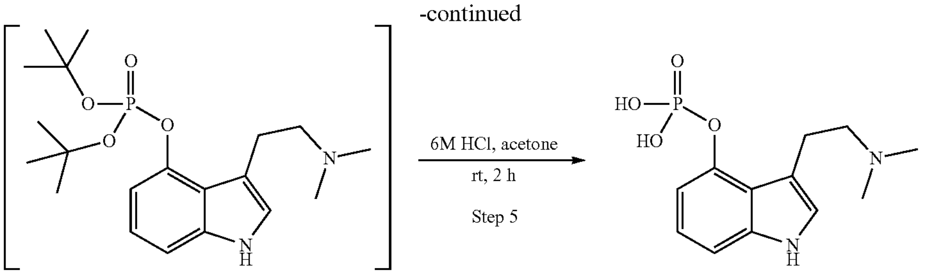

VI

Psilocybin (I)

Step 1: 3-(2-chloro-2-oxoacetyl)-1H-indol-4-yl 2-chloro-2-oxoacetate (Compound of Formula IV)

3.0 equivalents of oxalyl chloride was added to a diethyl ether solution of unprotected 4-hydroxyindole, at a temperature of 0° C. for and stirred 16 hours, to provide 3-(2-chloro-2-oxoacetyl)-1H-indol-4-yl 2-chloro-2-oxoacetate (IV) (See HPLC, same as FIG. 1)

Step 2: 2-(4-hydroxy-1H-indol-3-yl)-N,N-dimethyl-2-oxoacetamide (Compound of Formula V)

Excess (5.0 equivalents) of dimethylamine hydrochloride was added to a diethyl-ether/pyridine solution of crude 3-(2-chloro-2-oxoacetyl)-1H-indol-4-yl 2-chloro-2-oxoacetate of (2), at room temperature for 30 minutes, to provide exclusively 2-(4-hydroxy-1H-indol-3-yl)-N,N-dimethyl-2-oxoacetamide (V).

HPLC: Same as FIG. 2, $^1$H NMR (300 MHz, DMSO-D6): Same as FIG. 3

Step 3: 3-(2-(dimethylamino)ethyl)-1H-indol-4-ol (Psilocin, Compound of Formula II)

2 equivalents of lithium aluminum hydride ($LiAlH_4$) solution 1.0 M in tetrahydrofuran (THF) was added to a THF solution of 2-(4-hydroxy-1H-indol-3-yl)-N,N-dimethyl-2-oxoacetamide (V) under THF reflux for 4 hours, to provide 3-(2-(dimethylamino)ethyl)-1H-indol-4-ol (psilocin).

$^1$H NMR (300 MHz, DMSO-D6): same as FIG. 4

Step 4: di-tert-butyl (3-(2-(dimethylamino)ethyl)-1H-indol-4-yl) phosphate (Compound of Formula VI)

1.1 equivalents of di-tert-butylphosphite was added to sodium hydroxide (2.0 eq.) in a solution of carbon tetrachloride (0014) and tetrahydrofuran (THF), 1:1 v/v, for 16 hours at room temperature to yield crude di-tert-butyl (3-(2-(dimethylamino)ethyl)-1H-indol-4-yl) phosphate.

Step 5: Psilocybin 6M hydrogen chloride (HCl) in acetone was added to the crude di-tert-butyl (3-(2-(dimethylamino)ethyl)-1H-indol-4-yl) phosphate; (ii) the reaction mass was stirred at room temperature and maintained at room temperature for 2 hours; (iii) the reaction mass was then neutralized to pH 6-7 with a base; (iv) liberated impurities were removed from the reaction mass by extraction into an organic solvent; (v) crude psilocybin base was extracted into an organic solvent; (vi) solvent was distilled and crude psilocybin in an organic solvent was provided; crude psilocybin solution was isolated by filtration; (vii) crude psilocybin is dissolved in water medium and neutralized with a weak acid; (viii) pure psilocybin base is extracted into a solvent; (ix) the solvent is partially distilled and psilocybin is crystallized from same solvent; and (x) pure psilocybin is isolated by filtration.

Figure 6:
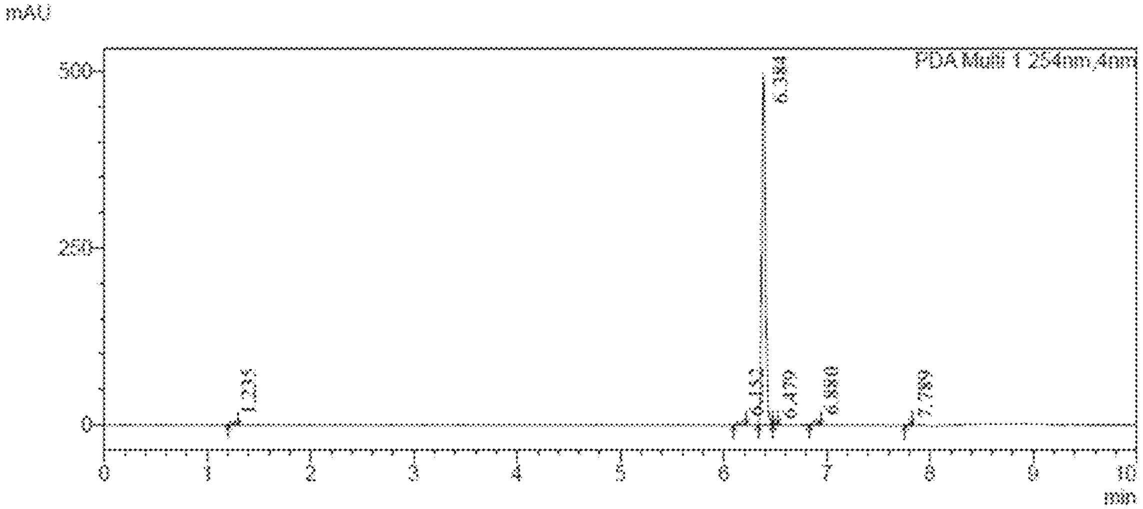
FIG. 6 is an HPLC chromatogram of psilocybin (compound of Formula I).
Figure 7:
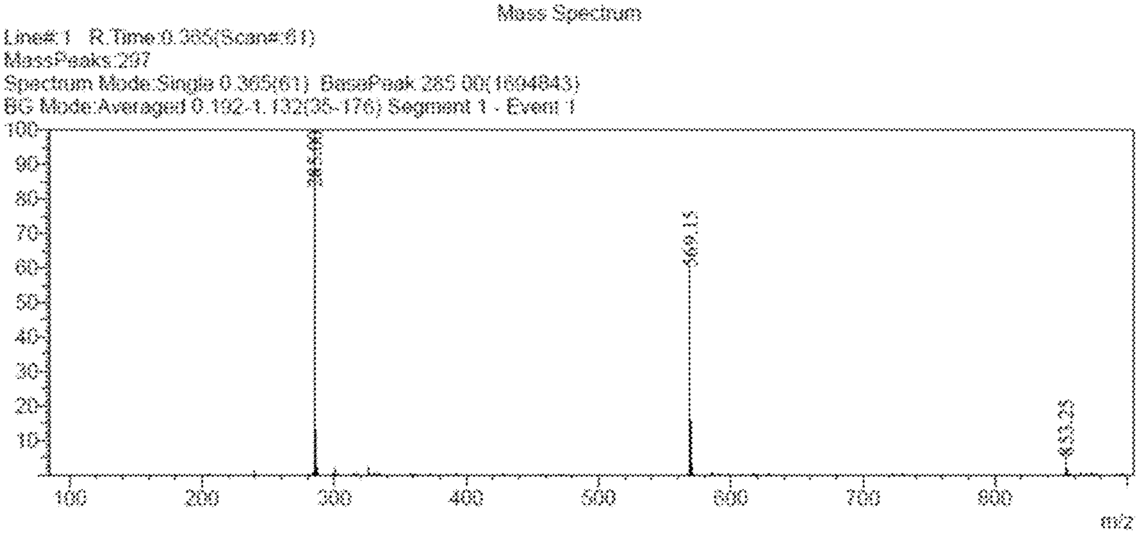
FIG. 7 is a mass spectrum of psilocybin (compound of Formula I).
Figure 8:
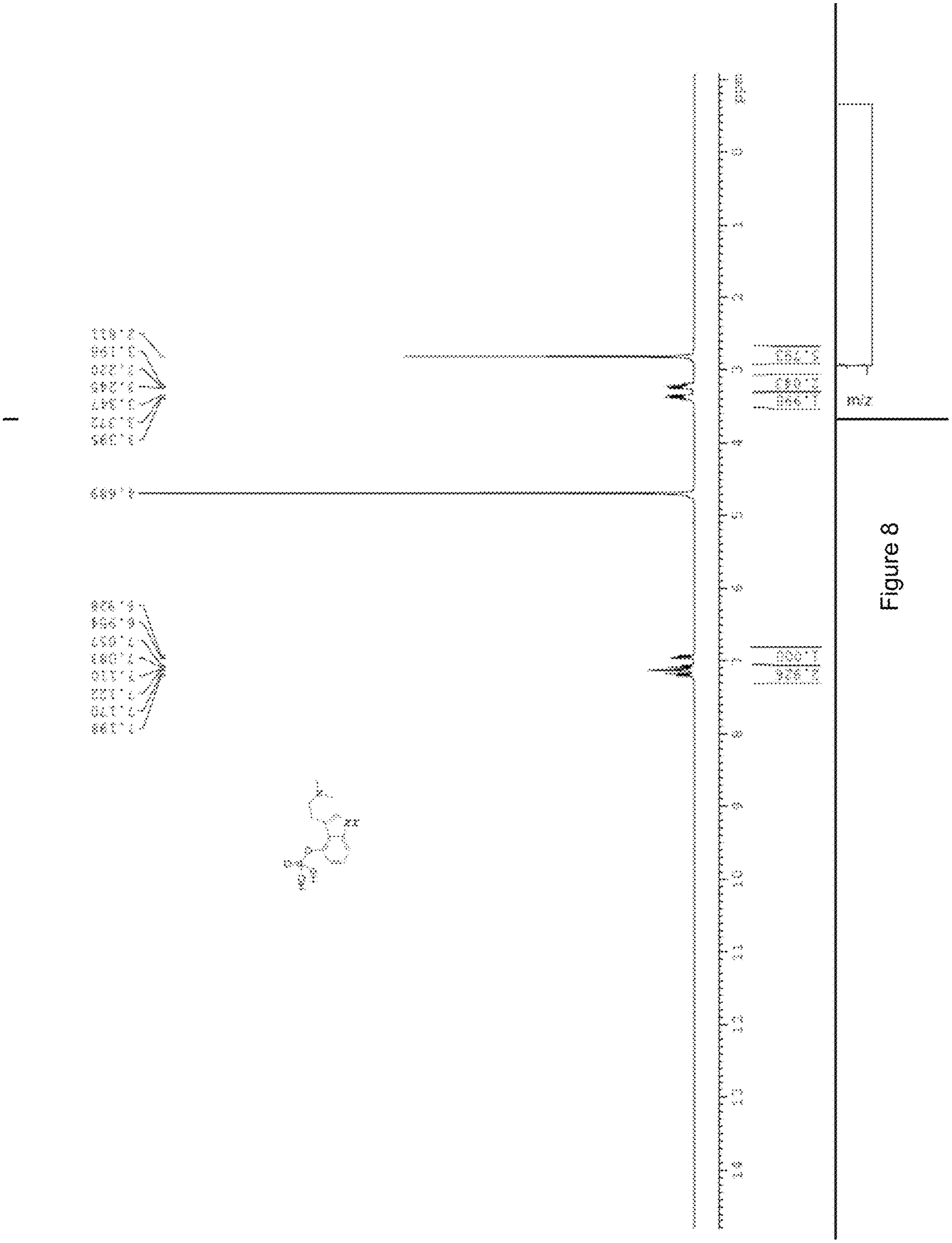
FIG. 8 shows a $^1$H NMR spectrum of psilocybin (compound of Formula I).

Product from step (vi): HPLC: Same as FIG. 6; Mass spectrum: Same as FIG. 7; $^1$H NMR (300 MHz, $CDCl_3$) Same as FIG. 8).

Example 3: Optimization of Preparation of di-tert-butyl (3-(2-(dimethylamino)ethyl)-1H-indol-4-yl) phosphate in the Presence of a Base

TABLE 1

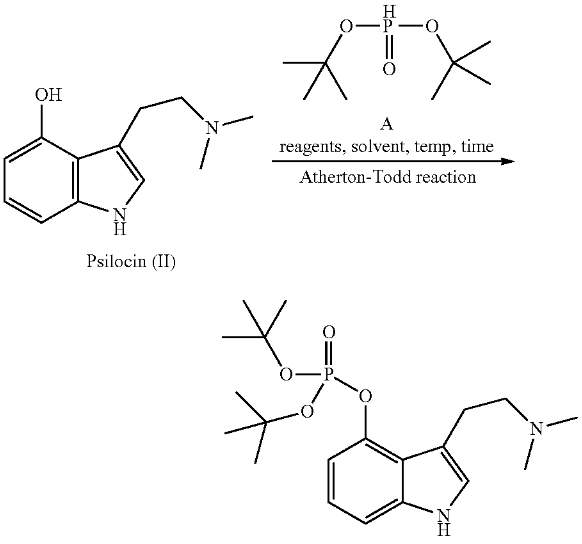

Psilocin (II)

(VI)

| Entry | Reagent | Base | Solvent | Temperature | Time | Product (yield % on LCMS, 24 nm) |
|---|---|---|---|---|---|---|
| 1 | A (1.1 eq) | TEA (2.0 eq) | $CCl_4$/MeCN/ $CHCl_3$ (1:1:1) | rt-50° C.-80° C. | 16 h | Major product: Psilocin (II) |
| 2 | A (1.1 eq) | DIEA (2.0 eq) | $CCl_4$/MeCN/ $CHCl_3$ (1:20:20) | rt-50° C.-80° C. | 16 h | Major product: Psilocin (II) |
| 3 | A (1.1 eq) | TEA (2.0 eq) | $CCl_4$ | rt-50° C.-80° C. | 16 h | Major product: Psilocin (II) |
| 4 | A (1.1 eq) | DABCO (1.5 eq) | $CCl_4$/RHF (1:1) | rt-50° C.-80° C. | 16 h | Major product: Psilocin (II) |
| 5 | A (1.1 eq) | DBU (2.0 eq) | $CCl_4$/DMSO (1:1) | rt-50° C.-80° C. | 16 h | Major product: Psilocin (II) |

TABLE 1-continued

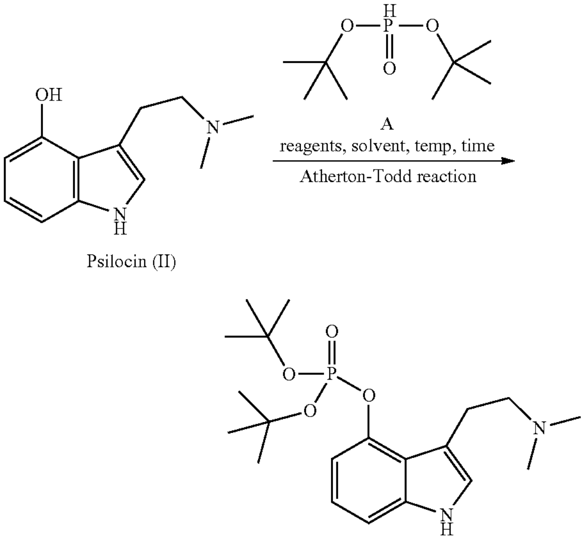

Psilocin (II)

(VI)

| Entry | Reagent | Base | Solvent | Temper-ature | Time | Product (yield % on LCMS, 24 nm) |
|---|---|---|---|---|---|---|
| 6 | A (1.1 eq) | NaOH (2.0 eq) | $CCl_4$/THF (1:1) | rt-50° C. | 16 h | Major product: VI |
| 7 | A (1.1 eq) | NaOH (2.0 eq)/ DMAP (0.1 eq) | $CCl_4$/THF (1:1) | rt-50° C. | 16 h | Major product: VI |

The reaction of psilocin with di-tert-butylphosphite in the presence of various bases. Table 1 shows that the reaction of psilocin with di-tert-butylphosphite in the presence of sodium hydroxide, or sodium hydroxide with DMAP provided (3-(2-(dimethylamino)ethyl)-1H-indol-4-yl) phosphate as the major product in a solvent mixture of carbon tetrachloride and tetrahydrofuran (THF).

Example 4: Exemplary Phosphorylation of Indole Using Chloro Di-Tert-Butyl Phosphite Di-tert-butyl phosphite was dissolved in 5V of THF, and added to 1.2 eq of N-chlorosuccinimide (NCS)/5V THF at 5° C. to generate chloro di-tert-butyl phosphite in situ. Unprotected 4-hydroxyindole was treated with lithium diisopropylamide and a catalytic am of DMAP in THF at 0° C. followed by the dropwise addition of the crude chloro di-tert-butyl phosphite provide corresponding di-tert-butyl 1H-indol-4-yl phosphate.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

What is claimed is:

1. A process for preparing psilocybin (compound of Formula I),

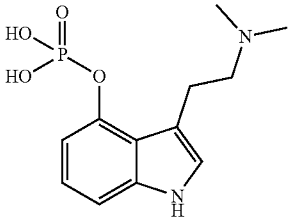

(I)

the process comprising:

reacting psilocin (compound of Formula II):

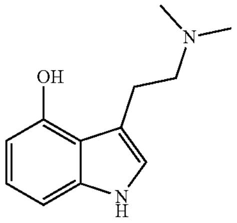

(II)

with (a) di-tert-butylphosphite,

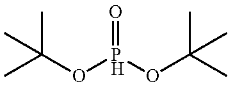

in the presence of a base or (b) chloro di-tert-butylphosphite,

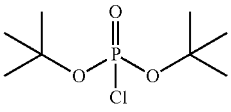

to provide a compound of Formula (VI):

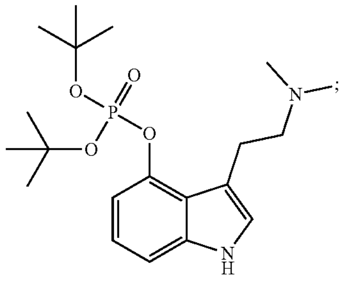

(VI)

;

and hydrolyzing the compound of Formula VI to provide the psilocybin (compound of Formula I).

2. The process of claim 1, wherein the psilocin is reacted with di-tert-butylphosphite in the presence of a base under Atherton-Todd reaction conditions to provide the compound of Formula (VI).

3. The process of claim 1, wherein the psilocin is reacted with about 1.1 to 1.5 molar equivalents of the di-tert-butylphosphite in the presence of an excess of base in an inert solvent at a temperature and for a time for reacting the psilocin with the di-tert-butylphosphite to provide the compound of Formula (VI).

4. The process of claim 1, wherein the base is selected from sodium hydroxide or sodium hydroxide in combination with dimethylaminopyridine (DMAP).

5. The process of claim 1, wherein the psilocin is reacted with chloro di-tert-butylphosphite to provide a compound of Formula (VI).

6. The process of claim 5, wherein the chloro di-tert-butylphosphite is prepared in situ by reacting di-tert-butylphosphite with N-chloro succinimide (NCS) and the process comprises reacting psilocin with di-tert-butylphosphite and N-chloro succinimide (NCS) to provide a compound of Formula (VI).

7. The process of claim 1, wherein the compound of Formula (VI) is hydrolyzed to provide psilocybin using an acid.

8. The process of claim 1, wherein the compound of Formula (VI) is crude or not purified, or the compound of Formula (VI) is not isolated prior to hydrolyzing to provide psilocybin.

9. The process of claim 1, wherein the psilocin (II) is prepared using a process comprising:

reacting unprotected 4-hydroxyindole (compound of Formula III):

(III)

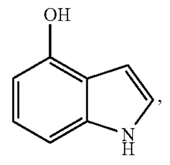

with oxalyl chloride to provide a compound of Formula (IV):

(IV)

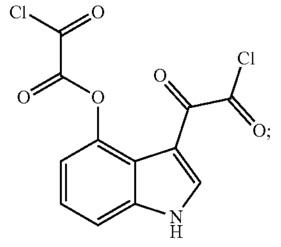

reacting the compound of Formula (IV) with dimethylamine ($HN(CH_3)_2$) to provide a compound of Formula (V):

(V)

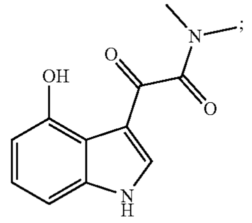

and reducing the compound of Formula (V) with a reducing reagent to provide psilocin (compound of Formula II).

10. The process of claim 4, wherein the psilocin is reacted with di-tert-butylphosphite at 18° C. to 50° C. for 2 hours to 8 hours.

11. The process of claim 3, wherein the inert solvent is a mixture of tetrahydrofuran and carbon tetrachloride.

12. The process of claim 1, further comprising preparing the psilocin (compound of Formula II), (II)

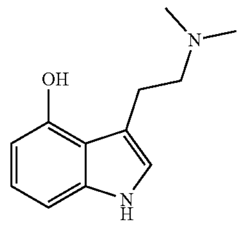

the process comprising:

reacting unprotected 4-hydroxyindole (compound of Formula III):

(III)

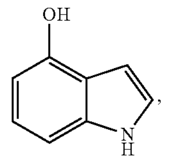

with oxalyl chloride to provide a compound of Formula (IV):

(IV)

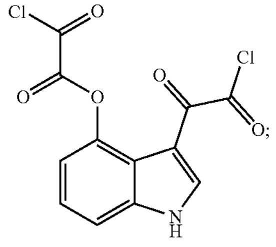

reacting the compound of Formula (IV) with dimethylamine ($HN(CH_3)_2$) to provide a compound of Formula (V):

(V)

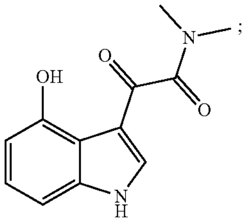

and reducing the compound of Formula (V) with a reducing reagent to provide psilocin (compound of Formula II);

(III)

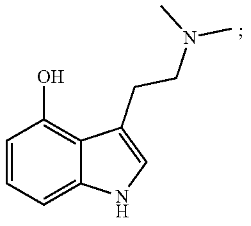

wherein said reacting psilocin comprises reacting psilocin with the di-tert-butylphosphite,

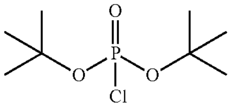

in the presence of the base to provide the compound of Formula (VI).

13. The process of claim 12, wherein the psilocin is reacted with di-tert-butylphosphite in the presence of sodium hydroxide or a combination of sodium hydroxide with 4-dimethylaminopyridine (DMAP) in a mixture of tetrahydrofuran and carbon tetrachloride to provide a compound of Formula (VI).

14. The process of claim 1, further comprising preparing psilocin (compound of Formula II), (II)

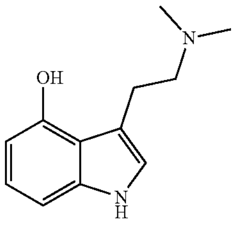

the process comprising:

reacting unprotected 4-hydroxyindole (compound of Formula III):

(III)

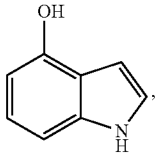

with an excess amount of oxalyl chloride to provide a compound of Formula (IV):

(IV)

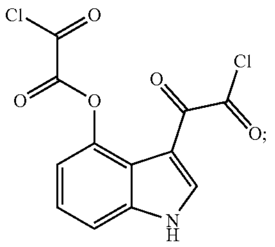

reacting the compound of Formula (IV) with an excess amount of dimethylamine to provide a compound of Formula (V):

(V)

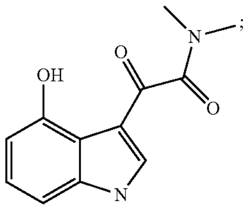

and reducing the compound of Formula (V) with a reducing reagent to provide psilocin (compound of Formula II);

(II)

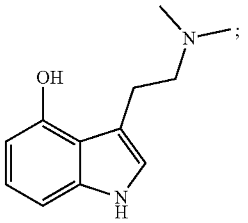

wherein said reacting psilocin comprises reaction of the psilocin with chloro di-tert-butylphosphite,

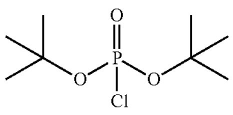

to provide a compound of Formula VI.

15. The process of claim 14, wherein the chloro di-tert-butylphosphite is prepared in situ by reacting di-tertbutylphosphite with N-chloro succinimide (NCS) and the process comprises reacting psilocin with di-tert-butylphosphite and N-chloro succinimide (NCS) to provide a compound of Formula (VI).

16. The process of claim 12, wherein the unprotected 4-hydroxyindole (III) is reacted with the oxalyl chloride in an inert solvent for a temperature and a time for the reaction of the unprotected 4-hydroxyindole with oxalyl chloride to provide the compound of Formula (IV).

17. The process of claim 16, wherein the unprotected 4-hydroxyindole (III) is reacted with 2 to 3 molar equivalents of the oxalyl chloride and the temperature and time for reacting the unprotected 4-hydroxyindole (III) with the oxalyl chloride to provide the compound of Formula (IV) is 0° C. to 15° C., for 6 hours to 24 hours.

18. The process of claim 16, wherein the unprotected 4-hydroxyindole (III) is reacted with 2 to 3 molar equivalents of the oxalyl chloride in MBTE and the temperature and time for reacting the unprotected 4-hydroxyindole (III) with the oxalyl chloride to provide the compound of Formula (IV) is 0° C. to 10° C. for 2 hours to 3 hours to provide the compound of Formula (IV).

19. The process of claim 12, wherein the dimethylamine ($N(CH_3)_2$) is generated in situ by reacting a dimethylamine acid salt with a base and the compound of Formula (IV) is reacted with the dimethylamine acid salt in the presence of the base to provide the compound of Formula (V).

20. The process of claim 19, wherein the compound of Formula (IV) is reacted with an excess amount of the dimethylamine acid salt in the presence of the base in an inert solvent for a temperature and a time for the compound of Formula (IV) to provide the compound of Formula (V).

21. The process of claim 20, wherein the temperature and time for reacting the compound of Formula (IV) with the dimethylamine acid salt in the presence of the base to provide the compound of Formula (V) is 18° C. to 25° C. for 15 minutes to 2 hours.

22. The process of claim 12, wherein the dimethylamine is dimethylamine free base.

23. The process of claim 22, wherein the compound of Formula (IV) is reacted with 2 to 6 molar equivalents of the dimethylamine and 2 to 4 molar equivalents of base to provide the compound of Formula (V).

24. The process of claim 12, wherein the compound of Formula (V) is reacted with 1.5 to 3 molar equivalents of the reducing agent in an inert solvent at a temperature and a time for reducing the compound of Formula (V) with the reducing agent to provide the psilocin (II).

* * * * *